US006271207B1

(12) United States Patent
Cristiano et al.

(10) Patent No.: US 6,271,207 B1
(45) Date of Patent: Aug. 7, 2001

(54) ENHANCED EXPRESSION OF TRANSGENES

(75) Inventors: Richard J. Cristiano, Pearland, TX (US); Dao Nguyen, Potamac, MD (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/175,056

(22) Filed: Oct. 19, 1998

Related U.S. Application Data

(63) Continuation of application No. PCT/US97/05325, filed on Apr. 1, 1997.
(60) Provisional application No. 60/015,790, filed on Apr. 17, 1996.

(51) Int. Cl.[7] .................................................. A61K 48/00
(52) U.S. Cl. ........................ 514/44; 435/320.1; 435/455; 435/458; 424/93.2
(58) Field of Search ............................... 514/44, 449, 27; 424/93.2, 649; 435/455, 458, 320.1, 325, 69.1; 378/69, 65

(56) References Cited

U.S. PATENT DOCUMENTS

| 5,399,346 | 3/1995 | Anderson et al. | 424/93.21 |
| 5,604,090 | * 2/1997 | Alexander et al. | 435/5 |
| 5,747,469 | * 5/1998 | Roth et al. | 514/44 |

FOREIGN PATENT DOCUMENTS

WO 95/33824   12/1995  (WO).

OTHER PUBLICATIONS

Cancerlit Database, AN 97604990, Zeng et al., Pro. Annu Meet Am Assoc Cancer Res, vol. 37, pp. A2345, abstract, 1996.*
Cancerlit Database, AN 97604989, Cerniglia et al., Pro. Annu Meet Am Assoc Cancer Res, vol. 37, pp. A2344, abstract, 1996.*
Cancerlit Database, AN 96601955, Stevens et al., Pro. Annu Meet Am Assoc Res, vol. 36, pp. A2518, abstract, 1995.*
Baichwal and Sugden, "Vectors for gene transfer derived from animal DNA viruses: Transient and stable expression of transferred genes", In: Kucherlapati R, ed. Gene transfer. New York: Plenum Press, pp. 117–148, 1986.
Bargonetti et al., "Wild–type but not mutant p53 immunopurified proteins bind to sequences adjacent to the SV40 origin or replication," *Cell*, 65:1083–1091, 1991.
Benvenisty and Neshif, "Direction introduction of genes into rats and expression of the genes", *Proc. Nat'l Acad. Sci. USA*, 83:9551–9555, 1986.
Bitter et al., "Expression and secretion for yeast", *Methods in Enzymol.*, 153:516–544, 1987.
Casey et al., "Growth suppression of human breast cancer cells by the introduction of a wild–type p53 gene", *Oncogene*, 6:1791–1797, 1991.

Chang et al., "Foreign gene delivery and expreddion in hepatocytes using a hepatitis B virus vector", *Hepatology*, 14:134A, 1991.
Chen and Okayama, "High–efficiency transfection of mammalian cells by plasmid DNA", *Mol. Cell Biol.*, 7:2745–2752, 1987.
Coffin, "Retroviridae and their replication", *In: Virology*, Fields et al. (eds.), New York: Raven Press, pp. 1437–1500, 1990.
Couch et al., "Immunization with types 4 and 7 adenovirus by selective infection of the intestinal tract", *Am. Rev. Resp. Dis.*, 88:394–403, 1963.
Coupar et al., "A general method for the construction of recombinant vaccinia virus expressing multiple foreign genes", *Gene*, 68:1–10, 1988.
Cusack et al., "High levels of gene transduction in human lung tumors following intralesional injection of recombinant adenovirus," *Cancer Gene Ther.*,3(4):345–249, 1996.
Diller et al., "p53 Functions as a Cell Cycle Control Protein in Osteosarcomas", *Mol. Cell Biol.*, 10(11):5772–5781, 1990.
Dubensky et al,. "Direct transfection of viral and plasmid DNA into the liver or spleen of mice", *Proc. Nat. Acad. Sci. USA*, 81:7529–7533, 1984.
Eastman, "Activation of programmed cell death by anticancer agents: cisplatin as a model system," *Cancer Cells*, 2:275–280, 1990.
Fechheimer et al., "Transfection of mammalian cells with plasmid DNA by scrape loading and sonication loading", *Proc. Nat'l Acad. Sci. USA*, 84:8463–8467, 1987.
Ferkol et al., "Regulation of the phosphoenolpyruvate carboxykinase/human factor IX gene introduced into the livers of adult rats by receptor–mediated gene transfer," *FASEB J.*, 7:1081–1091, 1993.
Fields et al., "Presence of a potent transcription activating sequence in the p53 portein," *Science*, 249:1046–1049, 1990.
Fraley et al., "Entrapment of a bacterial plasmid in phospholipid vesicles: Potential for gene transfer", *Proc. Nat'l Acad. Sci. USA*, 76:3348–3352, 1979.

(List continued on next page.)

*Primary Examiner*—Dave Trong Nguyen
(74) *Attorney, Agent, or Firm*—Fulbright & Jaworski

(57) ABSTRACT

The present invention provides for improved methods of gene transfer, both in vitro and in vivo. By treating neoplastic cells with a DNA-damaging agent prior to transduction with a transgene, the expression of the transgene is improved up to about 3-fold over the expression seen in the absence of the DNA-damaging agent treatment. This effect is not dependent on the tumor cell type, the method of DNA transduction or type of DNA-damaging agent. The effect is most dramatic when the transduction is performed about 1–3 days following treatment with the DNA-damaging agent.

10 Claims, 11 Drawing Sheets

OTHER PUBLICATIONS

Freshney, "Animal Cell Culture: A Practical Approach", Second Edition, Oxford/New York, IRL Press, Oxford University Press, 1992.

Friedmann, "Progress toward human gene therapy", Science, 244:1275–1281, 1989.

Fritsche et al., "Induction of nuclear accumulation of the tumor–suppressor protein p53 by DNA–damaging agents", Oncogene, 8:307–318, 1993.

Gavrieli et al., "Identification of Programmed Cell Death In Situ Via Specific Labeling of Nuclear DNA Fragmentation", J. Cell Biol., 119:493–501, 1992.

Ghosh and Bachhawat, "Targeting of liposomes to hepatocytes", In: Wu G. and C. Wu ed. Liver diseases, targeted diagnosis and therapy using specific receptors and ligands. New York: Marcel Dekker, pp. 87–104, 1991.

Ghosh–Choudhury, et al., "Protein IX, a minor component of the human adenovirus capsid, is essential for the packaging of full length genomes", EMBO J., 6:1733–1739, 1987.

Gomez–Foix et al., "Adenovirus–mediated transfer of the muscle glycogen phosphorylase gene into hepatocytes confers altered regulation of glycogen", J. Biol. Chem., 267:25129–25134, 1992.

Goodman and Gilman's "The Pharmacological Basis of Therapeutics." 8th ed. Pergammon Press, New York, 1990.

Gopal, "Gene transfer method for transient gene expression, stable transfection, and cotransfection of suspension cell cultures", Mol. Cell Biol., 5:1188–1190, 1985.

Graham and Prevec, "Manipulation of adenovirus vectors." In: E.J. Murray (ed.), Methods in Molecular Biology, Gene Transfer and Expression Protocols, New Jersey: The Humana Press Inc., 109–128, 1991.

Graham and Van Der Eb, "A new technique for the assay of infectivity of human adenovirus 5 DNA", Virology, 52:456–467, 1973.

Graham, et al., "Characteristics of a human cell line transformed by DNA from human adenovirus type 5", J. Gen Virol. 36:59–72, 1977.

Harland and Weintraub, "Translation of mammalian mRNA injected into Xenopus oocytes is specifically inhibited by antisense RNA", J. Cell Biol., 101:1094–1099, 1985.

Hermonat and Muzycska, "Use of adenoassociated virus as a mammalian DNA cloning vector: Transduction of neomycin resistance into mammalian tissue culture cells", Proc. Nat'l Acad. Sci. USA, 81:6466–6470, 1984.

Hersdorffer et al., "Efficient gene transfer in live mice using a unique retroviral packaging line", DNA Cell Biol., 9:717–723, 1990.

Herz and Gerard, "Adenovirus–mediated transfer of low density lipoprotein receptor gene acutely accelerates cholesterol clearance in normal mice", Proc. Nat'l Acad. Sci. USA 90:2812–2816, 1993.

Hollstein et al., "p53 mutations in human cancers", Science, 253:49–53, 1991.

Horwich et al., "Synthesis of hepadenovirus particles that contain replication–defective duck hepatitis B virus genomes in cultured HuH7 cells", J. Virol., 64:642–650, 1990.

Jones and Shenk, "Isolation of deletion and substitution mutants of adenovirus type 5", Cell, 13:181–188, 1978.

Kaneda et al., "Increased expression of DNA cointroduced with nuclear protein in adult rat liver", Science, 243:375–378, 1989.

Karlsson et. al., "Stable gene trasnfer and tissue–specific expression of a human globin gene using adenoviral vectors," EMBO J., 5:2377–2385, 1986.

Kato et al., "Expression of hepatitis b virus surface antigen in adult rat liver", J. Biol. Chem., 266:3361–3364, 1991.

Kaufman, "Induction of endonucleolytic dna cleavage in human acute myelogenous leukemia cells by etoposide, camptothecin, and other cytotoxic anticancer drugs: a cauthionary note", Cancer Res., 49:5870–5878, 1989.

Klein et al., "High–velocity microprojectiles for delivering nucleic acids into living cells", Nature, 327:70–73, 1987.

Le Gal La Salle et al., "An adenovirus vector for gene transfer into neurons and glia in the brain", Science, 259:988–990, 1993.

Levrero et al., "Defective and nondefective adenovirus vectors for expressing foreign genes in vitro and in vivo", Gene, 101:195–202, 1991.

MacGregor et al., "Histochemical staining of clonal mammalian cell lines expressing E. coli beta galactosidase indicates heterogeneous expression of the bacterial gene," Somat Cell Mol. Genet., 13:253–265, 1987.

Mann et al., "Construction of a retrovirus packaging mutant and its use to produce helper–free defective retrovirus", Cell, 33:153–159, 1983.

Markowitz et al., "A safe packaging line for gene transfer: Separating viral genes on two different plasmids", J. Virol., 62:1120–1124, 1988.

Mercer, "Cell cycle regulation and the p53 tumor suppressor protein", Critic. Rev. Eukar. Gene Express. 2:251–263, 1992.

Mietz et al., "The transcriptional transactivation function of wild–type p53 is inhibited by SV40 large T–antigen and by HPV–16 E6 oncoprotein," EMBO J., 11:5013–5020, 1992.

Mizrahi, "Production of human interferons: An overview", Process Biochem., 18(4):9–12, 1983.

Mulligan, "The Basic Science of Gene Therapy", Science, 260:926–932, 1993.

Nguyen et al., "Gene therapy for lung cancer: Enhancement of tumor suppression by a comination of sequential systemic cisplatin and adenovirus–mediated p53 gene transfer," J. Thorac. Cardiovasc. Surg., 112(5):1372–1377, 1996.

Nguyen et al., "Enhancement of gene transduction in human carcinoma cells by DNA–damaging agents," Proceedings of the American Association of Cancer Research, 37:347, Abstract No. 2369, 1996.

Nguyen et al., "Gene therapy for lung cancer: Enhancement of tumor suppression by a combination of systemic cisplatin and adenovirus–mediated p53 gene transfer," Proceedings of the American Association of Cancer Research, 37:347–348, Abstract No. 2370, 1996.

Nicolas and Rubenstein, "Retroviral vectors", In: Vectors: A survey of molecular cloning vectors and their uses, Rodriguez and Denhardt (eds.), Stoneham: Butterworth, pp. 494–513, 1988.

Nicolau and Sene, "Liposome–mediated DNA transfer in eukaryotic cells", Biochem. Biophys. Acta, 721:185–190, 1982.

Nicolau et al., "Liposomes as carriers for in vivo gene transfer and expression", Methods Enzymol., 149:157–176, 1987.

Paskind et al., "Dependence of moloney murine leukemia virus production on cell growth", Virology, 67:242–248, 1975.

Perales et al., "Gene transfer in vivo: sustained expression and regulation of genes introduced into the liver by receptor–targeted uptake," *Proc. Natl. Acad. Sci. USA*, 91:4086–4090, 1994.

Phillips et al., *In: Large Scale Mammalian Cell Culture* (Feder, J. and Tolbert, W. R., eds.), Academic Press, Orlando, FL, U.S.A., pp. 87–95, 1985.

Ponder et al., "Mouse hepatocytes migrate to liver parenchyma and function indefinitely after intraslenic transplantation," *Proc. Natl. Acad. Sci. USA*, 88:1217–1221, 1991.

Potter et al., "Enhancer–dependent expression of human k immunoglobulin genes introduced into mouse pre–B lymphocytes by electroporation", *Proc. Nat'l Acad. Sci. USA*, 81:7161–7165, 1984.

Ragot et al., "Efficient adenovirus–mediated transfer of a human minidystrophin gene to skeletal muscle of mdx mice", *Nature*, 361:647–650, 1993.

Renan, "Cancer genes: current status, future prospects, and applicants in radiotherapy/oncology", *Radiother. Oncol.*, 19:197–218, 1990.

Ridgeway, "Mammalian expression vectors", In: Rodriguez RL, Denhardt DT, ed. Vectors: A survey of molecular cloning vectors and their uses. Stoneham: Butterworth, pp. 467–492, 1988.

Rippe et al., "DNA–mediated gene transfer into adult rat hepatocytes in primary culture", *Mol. Cell Biol.*, 10:689–695, 1990.

Rosenfeld et al., "Adenovirus–mediated transfer of a recombinant a1–antitrypsin gene to the lung epithelium in vivo", *Science*, 252:431–434, 1991.

Rosenfeld et al., "In vivo transfer of the human cystic fibrosis transmembrane conductance regulator gene to the airway epithelium", *Cell*, 68:143–155, 1992.

Roux et al., "A versatile and potentially general approach to the targeting of specific cell types by retroviruses: Application to the infection of human cells by means of major histocompatibility complex class I and class II antigens by mouse ecotropic murine leukemia virus–derived viruses", *Proc. Natl. Acad. Sci. USA*, 86:9079–9083, 1989.

Russell et al., "DNA synthesis and topoisomerase inhibitors increase transduction by adeno–associated virus vectors," *Proc. Natl. Acad. Sci. USA*, 92:5719–5723, 1995.

Shaw et al., "Induction of apoptosis by wild–type p53 in a human colon tumor–derived cell line," *Proc. Natl. Acad. Sci. USA*, 89:4495–4499, 1992.

Son & Huang, "Exposure of human ovarian carcinoma to cisplatin transiently ensitizes the tumor cells for liposome––mediated gene transfer," *Proc. Natl. Acad. Sci. USA*, 91:12669–12672, 1994.

Takahasi et al., "Wild–type but not mutant p53 suppresses the growth of human lung cancer cells bearing multiple genetic lesions", *Cancer Res.*, 52:2340–2343, 1992.

Temin, "Retrovirus vectors for gene transfer: Efficient integration into and expression of exogenous DNA in vertebrate cell genome", *In: Gene Transfer*, Kucherlapati (ed.), New York: Plenum Press, pp. 149–188, 1986.

Top et al., "Immunization with live types 7 and 4 adenovirus vaccines. II. Antibody response and protective effect against acute respiratory disease due to adenovirus type 7", *J. Infect. Dis.*, 124:155–160, 1971.

Tur–Kaspa et al., "Use of electroporation to introduce biologically active foreign genes into primary rat hepatocytes", *Mol. Cell Biol.*, 6:716–718, 1986.

Varmus et al., "Retroviruses as mutagens: Insertion and excision of a non–transforming provirus alter the expression of a resident transforming provirus", *Cell*, 25:23–36, 1981.

Wagner et al., "Antisense gene inhibition by oligonucleotides containing C–5 propyne pyrimidines," *Science*, 260:1510–1513, 1990.

Weinberg, "Tumor suppressor gene", *Science*, 254:1138–1146, 1991.

Wilcock and Lane, "Localization of p53, retinoblastoma and host replication proteins at sites of viral replication in herpes–invected cells," *Nature*, 349:429–431, 1991.

Wong et al., "Appearance of b–lactamase activity in animal cells upon liposome mediated gene transfer", *Gene*, 10:87–94, 1980.

Wu and Wu, "Receptor mediated in vitro gene transfections by a soluble DNA courier system", *J. Biol. Chem*, 262:4429–4432, 1987.

Wu and Wu, "Evidence for tareted gene delivery to HepG2 hepatoma cells in vitro", *Biochemistry*, 27:887–892, 1988.

Wu and Wu, "Liver–directed gene delivery" *Adv. Drug Delivery Rev.*, 12:159–167, 1993.

Yang et al., "In vivo and in vitro gene transfer to mammalian somatic cells by particle bombardment", *Proc. Nat'l Acad. Sci. USA*, 87:9568–9572, 1990.

Yonish–Rouach et al., "Wild–type p53 induces apoptosis of myeloid leukaemic cells that is inhibited by interleukin–6," *Nature*, 352:345–347, 1991.

Zakut–Houri et al., "Human p53 cellular tumor antigen: CDNA sequence and expression in COS cells," *EMBO J.*, 4:1251–1255, 1985.

Zelenin et al., "High–velocity mechanical DNA transfer of the chloramphenicol acetyltransferase gene into rodent liver, kidney and mammary gland cells in organ explants and in vivo", *FEBS Lett.*, 280:94–96, 1991.

Zhang et al., "Detection of Wild–type Contamination in a Recombinant Adenoviral Preparation by PCR™", *BioTechniques*, 18:444–447, 1995.

Zhang et al., "Safety Evaluation of Ad5CMV–p53 In Vitro and In Vivo", *Human Gene Ther.*, 6:155–164, 1995.

* cited by examiner

ENHANCED EXPRESSION OF TRANSGENES

This is a continuation of co-pending application Serial No. PCT/US97/05325, international filing date Apr. 1, 1997, and claims priority to U.S. provisional application 60/015,790, filed Apr. 17, 1996.

The government may own rights in the present invention pursuant to funding of research under NIH Grant No. CA66037-01.

BACKGROUND OF THE INVENTION

A. Field of the Invention

The present invention relates to the field of gene expression, generally, and more specifically it adduces the expression recombinant transgenes in host cells. The invention may be exploited in the production of recombinant proteins in vitro or in gene therapy in vivo.

B. Related Art

The ability to express foreign genes in host cells has become a pivotal tool in molecular biology. For example, expressing proteins in host cells in vitro can lead to the large scale production of the protein for use in research or therapy. Examples of proteins that could be used in this manner are hormones, such as insulin, or cytokines, such as the interleukins. Scientists are constantly seeldng ways to maximize expression of tansgenes when they are imported into host cells.

Another important technology affected by foreign gene expression is gene therapy. Attaining high level expression in specific target cells is a key aspect of gene therapy, too. Numerous parameters have been varied in an effort to achieve higher levels of expression including the mode of gene trasduction, the vector, the promoter, as well as the dose and routes of administration.

Recently Son & Huang (1994) reported that exposure of CDDP-resistant ovarian carcinoma cells to CDDP prior to liposome-mediated gene transfer resulted in enhanced gene transduction. This study utilized an ovarian cancer cell line, 2008, that rapidly acquire CDDP-resistance following exposure. The cells in this study were exposed to CDDP for four to six weeks prior to gene transfer (in vitro) or exposed once, one week prior to gene transfer (in vivo). According to the authors, their data only indicate that CCDP-resistant cells show improved gene transduction. Thus, from this study, it is unclear whether CDDP-sensitive cells would provide the same results. It also is unclear whether the effect was tied to liposomal transfection methods, or could be more broadly applied.

A similar phenomenon has been observed in primary human foreskin fibroblasts infected with adeno-associated virus following brief exposure to high concentrations of CDDP or other DNA-damaging agents (Alexander et al., 1994; Russell et al., 1995). In this system, these non-malignant cells were rendered more susceptible to transduction by sublethal, but relatively high levels of DNA damaging agents. The treatments were conducted for 16 to 20 hours, followed immediately by transduction. The cause of the increased expression was not correlated with other transduction methodologies. Moreover, it was unclear from the data whether the treatment rendered the cells more competent for AAV transduction, whether increased uptake of AAV was induced or whether increased expression of AAV occurred following internalization.

Thus, it is clear that the prior art does not provide a clear picture, with respect to the effect of DNA-damaging agents, of their effects on the transduction and expression of transgenes in various host cells. There remains a need for a better understanding of these phenomena and for increasing the expression of transgenes in transduced cells.

SUMMARY OF THE INVENTION

It is, therefore, an object of the present invention to provide improved methods for expression of transgenes in host cells. This applies both to the in vitro and in vivo applications and includes a variety of different gene delivery systems, DNA-damaging agents, transgenes and target cells. More specifically, the invention provides for the enhancement of gene expression by providing a DNA damaging agent, preferably to a dividing cell, prior to administration of a vector containing a gene or genes of interest In one embodiment, the invention provides a method for enhancing the expression of a transgene comprising (a) contacting a target cell with a DNA-damaging agent; (b) removing the DNA-damaging agent from the target cell; and (c) transferring the transgene into the target cell between about 1–3 days after removing the DNA-damaging agent. More preferably, the tranfser of the gene occurs at about 2 days after removal. The target cell preferably is a dividing cell, and more preferably is a tumor cell.

The cell may be drug sensitive or drug insensitive.

The DNA-damaging agent is selected from the group consisting of cisplatin, carboplatin, VP16, teniposide, daunorubicin, doxorubicin, dactinomycin, mitomycin, plicamycin, bleomycin, procarbazine, nitrosourea, cyclophosphamide, bisulfan, melphalan, chlorambucil, ifosfamide, merchlorehtamine, and ionizing radiation.

Transfer of the transgene is accomplished by a technique selected from the group consisting of liposome-mediated transfection, receptor-mediated internalization and viral infection.

The transgene may be a tumor suppressor, such as p53. The transgene may be under the transcriptional control of a promoter, for example, the CMV IE promoter. Further, the trangene may have, in operable relation thereto, a polyadenylation signal, for example, the SV40 polyadenylation signal The transgene may be carried in an adenoviral vector.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1A:
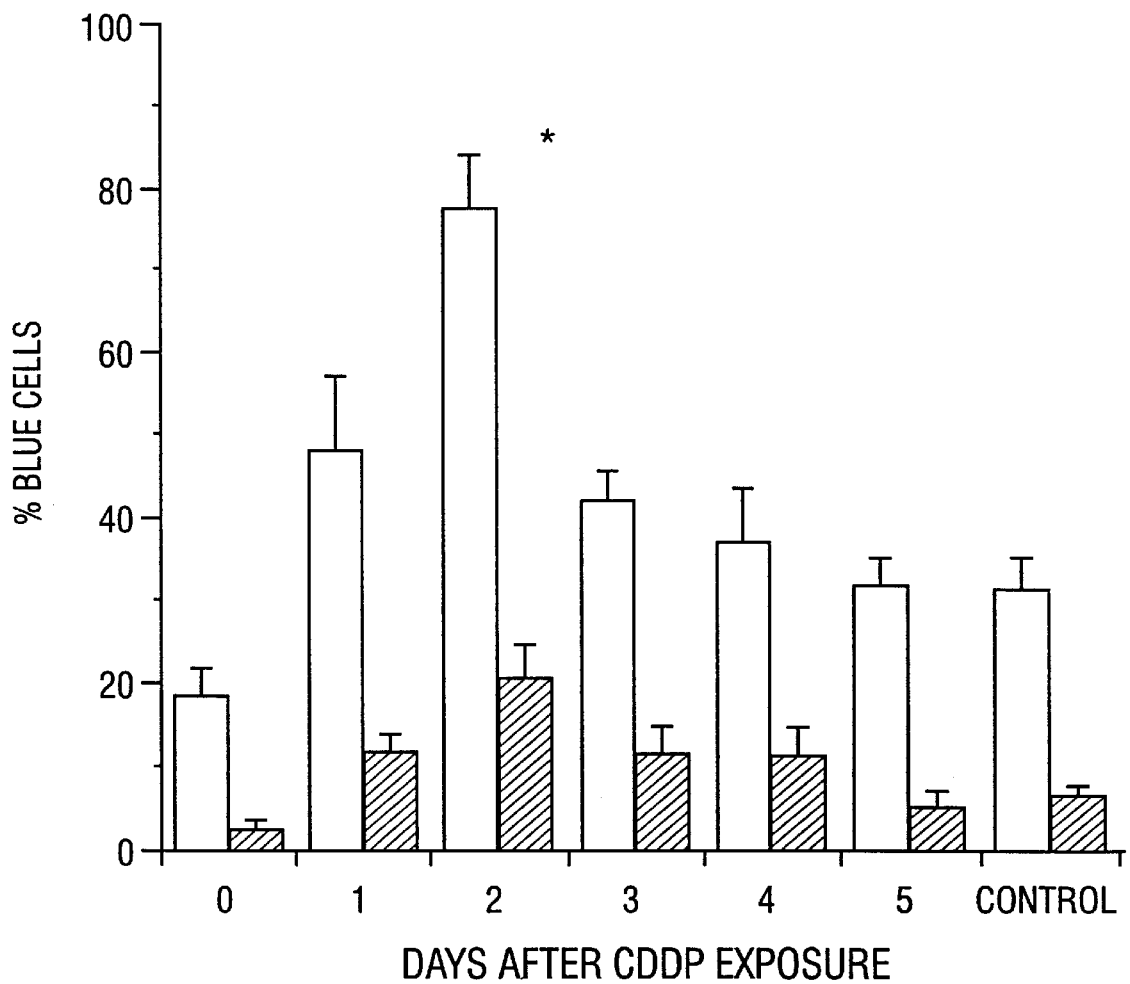
FIG. 1A—Time Course Analysis of CDDP Treatment. Time course of CDDP-induced enhancement of β-gal gene expression in H1299 (open bar) and H460 (hatched bar) cells in vitro. Maximal enhancement of β-gal gene expression was observed 2 days after exposure to CDDP (*=p<0.001 by ANOVA and Student's t test). Daily infection of untreated H1299 and H460 cells indicated that the transduction efficiency remained unchanged over the study period; mean±SD (day 0; immediately after removal of CDDP) (n=6; results of 2 experiments with triplicate samples). Cells were stained for β-gal expression 24 hrs after infection.

The present invention relies on the observation that treatment of neoplastic cells with DNA-damaging agents, prior to transduction with a transgene, results in the enhanced expression of the transgene. This effect is not observed when the cell is not neoplastic, i.e., when the cell exhibits normal growth control. Similarly, the effect is not observed when non-DNA-damaging anti-neoplastic agents are used. However, the effect does not appear to be limited to particular transgenes nor is it limited to particular transduction methodology, particular neoplastic cells or particular DNA-damaging agents. The invention is described in detail in the following sections.

A. Sequential Administration of a DNA-Damaging Agent and a Transgene

In accordance with the present invention, the methods provided for the enhancement of transgene expression are both time and order dependent. Each of these phenomena are discussed below and illustrated in the examples. These data should not be construed as indicating that time frames or orders outside the preferred embodiments of the present invention are inoperable; to the cony, data show that simultaneous administration of the p53 tumor suppressor gene in an adenoviral vector and cisplatin results in improved killing of tumor cells, when compared to treatment with the p53 adenoviral vector alone. It is the present inventors' observation, however, that using a particular order and using particular timing, transgene expression may be enhanced over that observed with other protocols.

As the data of the instant examples show, the prior treatment of host cells with a DNA-damaging, followed by provision of a transgene, results in improved expression of the transgene when compared to simultaneous or subsequent treatment with a DNA-damaging agent, or no DNA-damaging agent at all. In addition, there are particular time frames in which this effect is maximized. Preferably, the in vitro administration of the DNA-damaging agent precedes the transduction of the host cell by about 1–3 days (about 24–72 hrs) and, more preferably, about 2 days (about 48 hrs) after removal of the agent. In vivo, the time frame may be delayed somewhat, depending on the type and route of administration. Thus, it is suspected that a systemic administration of a chemotherapeutic should precede provision of the transgene by 2–4 days (about 48–96 hrs) and, more preferably, about 3 days (72 hrs).

Some minor variation in the optimal treatment times is expected depending on the tumor cell type, the particular transgene, the route of administration, the DNA-damaging agent or the delivery vector. To the extent that the skilled artisan desires, the optimal timing may be ascertained by performing time course experiments like those set out below in the examples to determine what times will provide the best expression in a given system. It is expected, however, that most will fall within the time frames set forth above.

B. DNA Damaging Agents

As stated above, the present invention relies on the ability of DNA-damaging agents to facilitate enhanced transgene expression in host cells. For the purposes of this application, DNA-damaging agents are defined as those agents that cause structural changes in DNA strands existing in the target cell at the time of. The following agents are provided as exemplary of DNA-damaging agents, as defined herein: cisplatin (CDDP), carboplatin, procarbazine, mechlorethamine, cyclophosphamide, ifosfamide, melphalan, chlorambucil, bisulfan, nitrosurea, dactinomycin, daunorubicin, doxorubicin, bleomycin, plicomycin, mitomycin, etoposide (VP16), and ionizing radiation. Other agents may be included as long as the adhere to the definition of DNA-damaging agents, provided above.

The following agents are not classified as DNA-damaging agents according to the present invention: transplatinum, 5-fluorouracil, vincristin, vinblastin and methotrexate.

Cisplatin (cis-dichlorodinminocisplatin; Mw=300.05) is a heavy metal compound used as a cancer chemotherapeutic. It has been applied to the treatment of testicular, ovarian, bladder and head/neck cancers. CDDP causes intra- and inter-strand crosslinking of DNA by forming guanine adducts and eventually DNA strand breaks (Eastman, 1990). CDDP is usually administered in 6–8 h periods with 1 liter of fluid and 25 to 50 mg of mannitol. The total dose administered usually is 40–120 mg/m$^2$ per therapy cycle, but depends on the frequency of cycles and individual tolerance. A common schedule is 20 mg/m$^2$/day for five days.

Carboplatin has a mechanism of action and spectrum of clinical activity similar to CDDP. It is often employed in treating recurrent ovarian cancer, including patients who have previously received cisplatin. Administration is an intravenous infusion over at least 15 min. The usual dose is 360 mg/$^2$, given once every four weeks.

Procarbazine, a methyl hydrazine derivative, is often used clinically against Hodgkin's disease, and also has shown activity against brain and lung tumors, non-Hodgkin's lymphoma, melanoma and myeloma. This drug induces chromosomal damage and chromatid breaks and translocations. The recommended oral daily dose for adults is 100 mg/m$^2$ for ten days in combination regimens.

Mechlorethamine is a nitrogen mustard that is used in treating Hodgkin's and other lymphomas. Among the effects observed with various nitrogen mustard agents is the opening of imidazole rings or depurination of bases in DNA, both of which can result in serious damage to the DNA strand.

The course of therapy consists of the injection of a total dose of 0.4 mg/kg or 10 mg/m$^2$. This total dose may be given in either two or four daily consecutive injections, a single administration is preferable. Direct intracavitary administration (0.2 to 0.4 mg/kg) for malignant effusions, particularly of pleural origin, is performed.

Cyclophosphamide, another nitrogen mustard, also alkylates DNA and results in damage to the strands. This drug has been used against Hodgkin's lymphoma, Burkitt's lymphoma and lymphoblastic leukemia. It can be administered orally, intravenously, intramuscularly, intrapleurally and intraperitoneally. A conservative daily dose of 2–3 mg/kg, orally or intravenously, is recommended for patients with more susceptible neoplasms such as lymphomas or leukemias. A higher dosage (4–8 mg/kg daily for six days followed by an oral maintenance dose of 1–5 mg/kg daily) has been used for the treatment of carcinomas and other more resistant neoplasms.

Melphalan is a phenylalanine derivative of nitrogen mustard. It has been used in the treatment of multiple myeloma, malignant melanoma and in carcinoma of the breast and ovary. The usual dose for multiple myeloma is 6 mg daily for a period of 2 to 3 weeks.

Ifosfamide is an analog of cyclophosphamide. It is currently approved for use in combination with other drugs for treatment of germ cell testicular cancer, and clinical trials have shown activity against carcinomas of the lung and cervix, Hodgkin's and non-Hodgkin's lymphomas, and certain sarcomas. The drug usually is infused intravenously over 30 min at a dose of 1.2 g/m$^2$ per day for five days. Patients should also receive at least 2 l of oral or intravenous fluid daily. Treatment cycles are usually repeated every three weeks.

Chlorambucil is an alkylating agent that has been used against chronic lymphocytic leukemia and primary macroglobulinemia. The standard initial daily dosage is 0.1 to 0.2 mg/kg, continued for at least 3 to 6 weeks. The total daily dose, usually 4 to 10 mg, is given at one time. Bisulfan is another alkylating agent that is used to treat chronic granulocytic leukemia Nitrosourea is clinically active against lymphomas, malignant melanomas, brain neoplasms and gastrointestinal carcinomas. Chemical decompositions yields reactive intermediates that form single-strand adducts with DNA and then, through a dehalogenation event, forms a second reactive site and cross-links DNA.

Dactinomycin is a antibiotic isolated from Steptomyces. In addition to blocking transcription, it induces single-strand breaks in DNA, possibly through a free-radical intermediate or as a result of topoisomerase II. It has been used against Hodgkin's and non-Hodgkin's lymphomas. The typical daily dose is 10 to 15 μg/kg/day intravenously for five days. Additional courses may be given at 3- to 4-week intervals in the absence of toxicity. Daily injections of 100 to 400 μg have been given to children for up to fourteen days. Weekly maintenance doses of 7.5 μg/kg have been used.

Daunorubicin is an anthracycline antibiotic that, among other actions, induces single- and double-stranded breaks. It is used against acute lymphocytic and acute granulocytic leukemias, acute non-lymphoblastic leukemias and certain lymphomas. The recommended dosage is 30 to 60 mg/m$^2$ daily for three days.

Doxorubicin is a hydroxy analog of daunorubicin, with activity against acute leukemias and malignant lymphomas; it also is active against a number of solid tumors, including breast cancer. The recommended dose is 60 to 75 mg/m$^2$, administered as a single intravenous infusion, repeated after 21 days.

Bleomycins are an important group of antitumor agents derived from *Streptomyces verticillus*. The currently used drug is a mixture of copper-chelating glycopeptides that consist primarily of two closely related agents, bleomycin $A_2$ and bleomycin $B_2$. They show a wide range of activity against a variety of tumors, including squamous carcinomas of the skin, head, neck and lungs, as well as against lymphomas and testicular tumors. Administration is a bolus dose of 15 units/m$^2$, twice a day for five days.

Plicamycin is a cytotoxic antibiotic isolated from cultures of *Streptomyces tanashiensis*. It has been used against advanced embryonal tumors of the testes. The recommended dosage for treatment of testicular tumors is 25 to 30 µg/kg daily or on alternate days for eight to ten doses. It usually is administered via intravenous infusion over 4 to 6 hours.

Mitomycin is an antibiotic isolated from *Steptomyces caespitosus*. The drug both inhibits DNA synthesis and cross-links DNA; single-strand breaks are induced by the removal of mitomycin. It is used in the palliative treatment of gastric adenocarcinoma, in conjunction with 5-FU and doxorubicin. It also has produced temporary benefits in carcinomas of the cervix, colon, rectum, pancreas, breast, bladder, head and neck, and lung, and in melanomas.

Etoposide (Mw=588.58) is a semi-synthetic derivative of podophyllotoxin with antineoplastic activity against testicular tumors and small-cell carcinoma of the lung, usually in combination with cisplatin. It also is active against non-Hodgkin's lymphomas, acute non-lymphocytic leukemia, carcinoma of the breast and Kaposi's sarcoma. Etoposide forms a tertiary complex between DNA and topoisomerase II and eventually produces protein-linked DNA single and double strand breaks (Kaufman, 1989). Intravenous dosage for testicular tumors is 50–100 mg/m$^2$ for five days, or 100 mg/m$^2$ on alternate days for three doses. For small-cell carcinoma, the dose is 35 mg/m$^2$ daily for four days to 50 mg/m$^2$ daily for five days. If given orally, the dosage should be doubled. Cycles of therapy are usually repeated every three to four weeks.

Teniposide is a thiophene derivative of etoposide that is used in the treatment of refractory acute lymphblastic leukemia in children. Administration is via intravenous infusion in doses that range from 50 mg/m$^2$ per day for five days to 165 mg/m$^2$ per day, twice weekly.

Radiation is an important tool in tumor therapy. Radiation falls into two major categories—electromagnetic radiation (waves of varying frequency, e.g., x-rays) and subatomic particle radiation (alpha, beta (electron), neutron, proton, meson and heavy ion). Gamma emissions are a form of electromagnetic radiation emitted from radioactive isotopes of radium, cobalt and other elements.

Radiation therapy transfers discrete energy units, called photons, to tissues causing damage to both normal and malignant cells. Ionizing irradiation stimulates production of oxygen free radicals which react with macromolecules and induces DNA damage (Cole et al., 1980). "Early" radiation effects include damage to proliferating cells, while "late" effects involve cell death and affect many different kinds of cells. Fortunately, radiation exploits the differential effects on malignant versus non-malignant cells, namely, that rapidly proliferating cells undergoing significant DNA synthesis suffer more severe effects from the DNA damage induced by radiation.

The dose of radiation is dependent upon tissue and tumor type. The treatment is usually fractionated to prevent toxicity and can be in the 1–5 Grey range over a several week period. For the treatment of rectal cancer radiation, 45 Grey total dose is given (1.8 Grey dose/day, Monday through Friday). For the enhancement of gene expression, a single dose of between 1 and 8 Grey is contemplated for gamma radiation

C. Transgenes and Expression Constructs

The transgenes of the present invention may encode any protein of interest.

Various proteins are useful for their biological activities in vitro and in vivo. For example, cytokines and hormones have already found use in treating certain diseases. For example, the interleukins (IL-1 to 11), interferon, human growth hormone, insulin, insulin-like growth factor, prolactin, placental lactogen, luteinizing hormone, follicle stimulating hormone, chorionic gonadotropic, thyroid-stimulating hormone, glucagon, somatostatin, calcitonin, vasopressin, vasostatin, vasotocin, gastrn, amylin, growth hormone releasing factor, growth hormone releasing hormone, luteinizing hormone releasing hormone, thymidine kinase, interleukin-1-beta converting enzyme and others are suitable subjects of the present invention.

In addition, the use of tumor suppressor genes such as p53, C-CAM, retinoblastoma gene, herpesvirus and p16 are candidates for gene transfer. These proteins act to regulate cell growth, and their reduction, mutation or deletion can affect the ability of cells to undergo normal cell senescence or apoptosis. Introducing transgenes encoding these proteins can reestablish normal cell growth, and expression of high levels of these proteins can even overcome defects in other genes that cause neoplastic proliferation.

p53 is a 53 kD nuclear phosphoprotein of 375 amino acids that controls cell proliferation. Mutations to the p53 gene, and allele loss on chromosome 17p, where this gene is located, are among the most frequent alterations identified in human malignancies. The p53 protein is highly conserved through evolution and is expressed in most normal tissues. Wild-type p53 has been shown to be involved in control of the cell cycle (Mercer, 1992), transcriptional regulation (Fields et al., 1990; Mietz et al, 1992), DNA replication (Wilcock and Lane, 1991; Bargonetti et al., 1991) and induction of apoptosis (Yonish-Rouach et al., 1991; Shaw et al., 1992).

Various mutant p53 alleles are known in which a single base substitution results in the synthesis of proteins that have quite different growth regulatory properties and, ultimately, lead to malignancies (Hollstein et al., 1991). In fact, the p53 gene has been found to be the most frequently mutated gene in common human cancers (Hollstein et al., 1991; Weinberg, 1991), and is particularly associated with those cancers linked to cigarette smoke (Hollstein et al., 1991; Zakut-Houri et al., 1985). The overexpression of p53 in breast tumors has also been documented (Casey et al., 1991).

Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Casey and colleagues have reported that transfection of DNA encoding wild-type p53 into two human breast cancer cell lines restores growth suppression control in such cells (Casey et al., 1991). A similar effect has also been demonstrated on transfection of wild-type, but not mutant, p53 into human lung cancer cell lines (Takahasi et al., 1992). The p53 appears dominant over the mutant gene and will select against proliferation when transfected into cells with the mutant gene. Normal expression of the transfected p53 does not affect the growth of cells with endogenous p53.

Alternatively, the transgenes may encode antisense oligonucleotides that hybridize, under intracellular conditions, to a target nucleic acid. The target nucleic acid may be a DNA molecule or an RNA molecule. Hybridization results in the inhibition of transcription and or translation of the protein encoded by the target nucleic acid The design of antisense constructs, based on the sequence of genes, will be evident to those of skill in the art The term "antisense nucleic acid" is intended to refer to the oligonucleotides complementary to the base sequences of a target DNA or RNA. Antisense oligonucleotides, when introduced into a target cell, specifically bind to their target nucleic acid and interfere with transcription, RNA processing, transport, translation and/or stability. Targeting double-stranded (ds) DNA with oligos or oligonucleotides leads to triple-helix formation; targeting RNA will lead to double-helix formation.

Antisense constructs may be designed to bind to the promoter and other control regions, exons, introns or even exon-intron boundaries of a gene. Antisense RNA constructs, or DNA encoding such antisense RNA's, may be employed to inhibit gene transcription or translation or both within a host cell, either in vitro or in vivo, such as within a host animal, including a human subject. Nucleic acid sequences which comprise "complementary nucleotides" are those which are capable of base-pairing according to the standard Watson-Crick complementarity rules. That is, that the larger purines will base pair with the smaller pyrimidines to form combinations of guanine paired with cytosine (G:C) and adenine paired with either thymine (A:T), in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

As used herein, the terms "complementary" or "antisense sequences" mean nucleic acid sequences that are substantially complementary over their entire length and have very few base mismatches. For example, nucleic acid sequences of fifteen bases in length may be termed complementary when they have a complementary nucleotide at thirteen or fourteen positions with only a single mismatch. Naturally, nucleic acid sequences which are "completely complementary" will be nucleic acid sequences which are entirely complementary throughout their entire length and have no base mismatches.

Other sequences with lower degrees of homology also are contemplated. For example, an antisense construct which has limited regions of high homology, but also contains a non-homologous region (e.g., a ribozyme) could be designed. These molecules, though having less than 50% homology, would bind to target sequences under appropriate conditions.

While all or part of the gene sequence may be employed in the context of antisense construction, statistically, any sequence of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that oligonucleotides of 8, 9, 10, 11, 12, 13, 14, 15, 16, 17, 18, 19, 20 or more base pairs will be used. One can readily determine whether a given antisense nucleic acid is effective at targeting of the corresponding host cell gene simply by testing the constructs in vitro to determine whether the endogenous gene's function is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

As an alternative to targeted antisense delivery, targeted ribozymes may be used. The term "ribozyme" is refers to an RNA-based enzyme capable of targeting and cleaving particular base sequences in target DNA and RNA. Ribozymes can either be targeted directly to cells, in the form of RNA oligonucleotides incorporating ribozyme sequences, or introduced into the cell as an expression construct encoding the desired ribozymal RNA. Ribozymes may be used and applied in much the same way as described for antisense nucleic acids. Ribozyme sequences also may be modified in much the same way as described for antisense nucleic acids. For example, one could incorporate non-Watson-Crick bases, or make mixed RNA/DNA oligonucleotides, or modify the phosphodiester backbone.

The term "cDNA" is intended to refer to DNA prepared using messenger RNA (mRNA)as template. The advantage of using a cDNA, as opposed to genomic DNA or DNA polymerized from a genomic, non- or partially-processed RNA template, is that the cDNA does not contain any non-coding sequences but, rather, contains only the coding region of the corresponding protein. There may be times when the full or partial genomic sequence is preferred, such as where the non-coding regions are required for optimal expression or where non coding regions such as introns are to be targeted in an antisense strategy.

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a gene and translation of a RNA into a gene product In other embodiments, expression only includes transcription of the nucleic acid, i.e., antisense and ribozymes.

In preferred embodiments, the nucleic acid is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally spealing, such a promoter might include either a human or viral promoter.

In various embodiments, the human cytomegalovirus (CMV) inmediate early gene promoter, the SV40 early promoter and the Rous sarcoma virus long terminal repeat can be used to obtain high-level expression of transgenes. The use of other viral or mammalian cellular or bacterial phage promoters which are well-known in the art to achieve expression of a transgene is contemplated as well, provided that the levels of expression are sufficient for a given purpose.

By employing a promoter with well-known properties, the level and pattern of expression following transfection can be optimized. For example, selection of a promoter which is active specifically in lung cells, such as tyrosinase (melanoma), alpha-fetoprotein and albumin (liver tumors), CC10 (lung tumor) and prostate-specific antigen (prostate tumor) will permit tissue-specific expression. Further, selection of a promoter that is regulated in response to specific physiologic signals can permit inducible expression. For example, with human PAI-1 promoter, expression is inducible by tumor necrosis factor. Tables 1 and 2 list several elements/promoters which may be employed, in the context of the present invention, to regulate the expression of a transgene. This list is not intended to be exhaustive of all the possible elements involved in the promotion of transgene expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a transgene in an expression construct (Table 1 and Table 2). Additionally any promoter/enhancer combination (as per the Eukaryotic Promoter Data Base EPDB) could also be used to drive expression of a transgene. Use of a T3, T7 or SP6 cytoplasmic expression system is another possible embodiment Eukaryotic cells can support cytoplasmic transcription from certain bacterial promoters if the appropriate bacterial polymerase is provided, either as part of the delivery complex or as an additional genetic expression construct.

TABLE 1

| PROMOTER |
| --- |
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| c-fos |
| c-HA-ras |
| Insulin |
| Neural Cell Adhesion Molecule (NCAM) |
| $\alpha_{1\text{-Antitrypsin}}$ |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retrovinises |
| Papilloma Virus |
| Hepatitis B Virus |
| Human Immunodeficiency Virus |
| Cytomegalovirus |
| Gibbon Ape Leukemia Virus |

TABLE 2

| Element | Inducer |
| --- | --- |
| MT II | Phorbol Ester (TFA) |
| | Heavy metals |

TABLE 2-continued

| Element | Inducer |
| --- | --- |
| MMTV (mouse mammary tumor virus) | Glucocorticoids |
| β-Interferon | poly(rI)X poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (CITA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |

Where a cDNA insert is employed, one will typically desire to include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal and the bovine growth hormone polyadenylation signal, convenient and known to function well in various target cells. Also contemplated as an element of the expression cassette is a terminator. These elements can serve to enhance message levels and to minimize read through from the cassette into other sequences.

Specific initiation signal also may be required for efficient translation of coding sequences. These signals include the ATG initiation codon and adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements (Bittner et al., 1987).

In preferred embodiments of the invention, the expression construct comprises a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986), adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kilobases of foreign genetic material but can be readily introduced in a variety of cell lines and laboratory animals (Nicolas and Rubenstein, 1988; Temin, 1986).

(i) Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene, termed Ψ, functions as a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a transgene is inserted into the viral genome in the place of certain viral sequences to produce a virus that is replication-defective. In order to produce virions, a packaging cell line containing the gag, pol, and env genes but without the LTR and Ψ components is constructed (Mann et al., 1983). When a recombinant plasmid containing a human cDNA, together with the retroviral LTR and Ψ sequences is introduced into this cell line (by calcium phosphate precipitation for example), the Ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retrovinuses is then collected, optionally concentrated, and used for gene tansfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact Ψ sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

One limitation to the use of retrovirus vectors in vitvo is the limited ability to produce retroviral vector titers greater than $10^6$ infectious U/mL. Titers 10- to 1,000-fold higher are necessary for many in vivo applications.

(ii) Adenovirus

Knowledge of the genetic organization of adenovirus, a 36 kB, linear and double-stranded DNA virus, allows substitution of a large piece of adenoviral DNA with foreign sequences up to 7 kB (Grunhaus and Horwitz 1992). In contrast to retrovirus, the infection of adenoviral DNA into host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in the human.

Adenovirus is particularly suitable for use as a gene transfer vector because of its mid-sized genome, ease of manipulation, high titer, wide target-cell range, and high infectivity. Both ends of the viral genome contain 100–200 base pair (bp) inverted terminal repeats (ITR), which are cis elements necessary for vital DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication These proteins are involved in DNA replication, late gene expression, and host cell shut off (Renan, 1990). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and all the mRNAs issued from this promoter possess a 5' tripartite leader (TL) sequence which makes them preferred mRNAs for translation.

In the current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure. Use of the YAC system is an alternative approach for the production of recombinant adenovirus.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham, et al., 1977). Since the E3 region is dispensable from the adenovirus genome (Jones and Shenk, 1978), the current adenovirus vectors, with the help of 293 cells, carry foreign DNA in either the E1, the E3 or both regions (Graham and Prevec, 1991). In nature, adenovirus can package approximately 105% of the wild-type genome (Ghosh-Choudhury, et al., 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1 deleted virus is incomplete. For example, leakage of viral gene expression has been observed with the currently available adenovirus vectors at high multiplicities of infection (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Other than the requirement that the adenovirus vector be replication defective, or at least conditionally defective, the nature of the adenovirus vector is not believed to be cmcial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the method of the present invention This is because Adenovirus type 5 is a human adenovirus about which a great deal of biochemical and genetic information is known, and it has historically been used for most constructions employing adenovirus as a vector.

As stated above, the typical adenoviral vector according to the present invention is replication defective and will not have an adenovirus E1 region. Thus, it will be most convenient to introduce the transgene nucleic acid into the position from which the E1 coding sequences have been removed. However, the position of insertion of the coding region within the adenovirus sequences is not critical to the present invention. The nucleic acid encoding a transcription unit also may be inserted in lieu of the deleted E3 region in E3 replacement vectors as described previously by Karlsson et. al. (1986) or in the E4 region where a helper cell line or helper virus complements the E4 defect Adenovirus is easy to grow and manipulate and exhibits broad host range in vitro and in vivo. This group of viruses can be obtained in high titers, e.g., $10^9$–$10^{11}$ plaque-forming unit (PFU)/ml, and they are highly infective. The life cycle of adenovirus does not require integration into the host cell genome. The foreign genes delivered by adenovirus vectors are episomal, and therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz 1992; Graham and Prevec, 1992). Recently, animal studies suggested that recombinant adenovirus could be used for gene therapy (Stratford-Perricaudet and Pernicaudet, 1991; Stratford-Perricaudet et al., 1990; Rich et al., 1993). Experiments in administering recombinant adenovirus to different tissues include trachea instillation (Rosenfeld et al., 1991; Rosenfeld et al., 1992), muscle injection (Ragot et al., 1993), peripheral intravenous injection (Herz and Gerard, 1993), and stereotactic inoculation into the brain (Le Gal La Salle et al., 1993). In addition to these protocols, the present invention also contemplates direct tumoral injection.

(iii) Other Viral Vectors as Expression Constructs

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesvises may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

D. Methods of Gene Transfer

In order to effect expression of sense or antisense transgene constructs, the expression construct must be delivered into a cell. This delivery may be accomplished in vitro, as in laboratory procedures for transforming cells lines, or in vivo or ex vivo, as in the treatment of certain disease states. As described above, the one mechanism for delivery is via viral infection where the expression consct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

In one embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky etal. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a transgene may also be transferred in a similar manner in vivo and express the corresponding protein.

Another embodiment of the invention for transferring a naked DNA expression construct into cells may involve particle bombardment This method depends on the ability to accelerate DNA coated microprojecfiles to a high velocity allowing them to pierce cell membranes and enter cells without killing them (Klein et al., 1987). Several devices for accelerating small particles have been developed One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, ie., ex vivo treatment Again, DNA encoding a transgene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a transgene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent Several ligands have been used for receptor-mediated gene transfer. The most extensively characterized ligands are asialoorosomucoid (ASOR) (Wu and Wu, 1987) and tansferrin (Wagner et al., 1990). Recently, a synthetic neoglycoprotein, which recognizes the same receptor as ASOR, has been used as a gene delivery vehicle (Ferkol et al., 1993; Perales et al., 1994).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a transgene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells, in vitro, and then the return of the modified cells back into an animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

During in vitro culture conditions, the expression construct delivers a nucleic acid to the cells and the protein is expressed. Finally, the cells may be reintroduced into the original animal, or administered into a distinct animal, in a pharmaceutically acceptable form by any of the means described below. Thus, providing an ex vivo method of treating a mammal with a pathologic condition is within the scope of the invention.

E. Recombinant Protein Production In Vitro

Another embodiment of the present invention involves the use of gene transfer to generate recombinant cells lines in vitro for the production of recombinant proteins. The gene of interest may be transferred as described above into appropriate host cells followed by culture of cells under the appropriate conditions. The gene for virtually any polypeptide may be employed in this manner. The generation of recombinant expression vectors, and the elements included therein, are discussed above.

Examples of useful mammalian host cell lines are Vero and HeLa cells and cell lines of Chinese hamster ovary, W138, BHK, COS-7, 293, HepG2, 3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, the herpes simplex virus thymidine kinase, hypoxanthine-guanine phosphoribosyltransferase and adenine phosphoribosyltransferase genes, in tk-, hgprt- or aprt- cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (ie., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon (Phillips et al., 1985; Mizrahi, 1983). Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

F. In Vivo Gene Therapy Applications

In another embodiment of the present invention, methods for improved gene therapy are provided. The present invention contemplates the use of gene therapeutic vectors, in conjunction with DNA-damaging agent treatment, to provide for high level expression of transgenes in vivo. This will be accomplished by treating an individual with an effective amount of a DNA damaging agent, followed by administration of a therapeutic gene. As stated above, the timing of the administration is important for achieving maximal enhancement of expression. The 1–3 day time period between administration of the DNA-damaging agent and administration of the transgene for in vitro may be delayed somewhat for in vivo applications, especially where the DNA-damaging agent is administered systematically. However, where the DNA-damaging agent is given locally to the site of administration of the transgene, the 1–3 window should be appropriate.

Administration of the DNA-damaging agent to patient will follow well-established protocols. For example, the administration of cisplatin would occur via intravenous infusion over about 8 hours with adequate prior hydration to minimize nephrotoxicity. The particular dose is dependent upon tumor type and size and the overall condition of the patient. The dose ranges from 60 mg/m$^2$ to 100 mg/m$^2$. Two to three days following cisplatin treatment, the vector system would be administered, for example, via intratumoral injection. It is anticipated that the treatment cycles would be repeated every four weeks as necessary.

Where clinical application of an expression construct comprising a nucleic acid encoding a transgene is contemplated, it will be necessary to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

Aqueous compositions of the present invention comprise an effective amount of the expression construct and nucleic acid, dissolved or dispersed in a pharmaceutically acceptable carrier or aqueous medium. Such compositions can also be refered to as inocula The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The expression constructs and delivery vehicles of the present invention may include classic pharmaceutical preparations. Administration of therapeutic compositions according to the present invention will be via any common route so long as the target tissue is available via that route. This includes oral, nasal, buccal, rectal, vaginal or topical. Topical administration would be particularly advantageous for treatment of skin cancers, to prevent chemotherapy-induced alopecia or other dermal hyperproliferative disorder. Alternatively, administration will be by orthotopic, intradermal subcutaneous, intramuscular, intraperitoneal or intravenous injection. Such compositions would normally be administered as pharmaceutically acceptable compositions that include physiologically acceptable carriers, buffers or other excipients.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsied. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations are suitable for oral administration Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

An effective amount of the therapeutic agent is determined based on the intended goal, for example, in the case of tumor therapy: (i) inhibition of tumor cell proliferation or (ii) elimination of tumor cells. The term "unit dose" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual.

G. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1: ENHANCEMENT OF GENE EXPRESSION IN HUMAN CARCINOMA CELLS BY DNA-DAMAGING AGENTS FOLLOWING GENE TRANSFER

Materials and Methods

Cells and Culture Conditions

The human non-small cell lung carcinoma cell lines H1299 and H460 were grown in RPMI-1640 medium supplemented with 5% heat-inactivated fetal calf serum (FCS), 10 mM glutamine, 100 units/ml of penicillin, 100 µg/ml of streptomycin and 0.25 µg/ml of amphotericin B.

Human non-small cell lung carcinoma cell lines H358, H226br, and the cervical cancer cell line SiHa were maintained in complete RPMI-1640 medium supplemented with 10% ECS. The cell line A549 (human, non-small cell lung carcinoma) was grown in Ham's F12 nutrient mixture solution (Gibco BRL, Gaithersburg, Md.) similarly supplemented with antibiotics, glutamine and 10% FCS. Primary normal human bronchial epithelial (NHBE) cells (Clonetics Corporation, San Diego, Calif.), were grown in serum-free optimized growth medium and subcultured under conditions suggested by the manufacturer.

In Vitro Characterization of the Effects of CDDP Exposure on β-gal Expression

Gene Delivery Protocol: In vitro gene delivery was performed by incubating cells in six-well plates (Falcon Plastics, Lincoln Park, N.J.) for two hours with Adv/CMV/β-gal in appropriate medium supplemented with 2% FCS. The multiplicity of infection (MOI: number of viral particles per target cell) was based on cell counts of untreated wells. Fresh, complete medium with the appropriate concentration of FCS was then added to the wells at the end of the infection period and cells were then incubated for 20 hours at 37° C., 5% $CO_2$. After washing the cells with ice cold PBS, the cells were fixed with ice-cold 1.25% glutaraldehyde and stained with X-gal (5-bromo-4-chloro-3-indolyl-β-d-galactoside; Gibco BRL) as previously described (MacGregor et al., 1987). The transduction efficiency by Adv/CMV/β-gal was determined by the percentage of positive stained cells (blue) for β-galactosidase activity (1000 cells counted per well).

Time Course and Dose Response: To determine the time course of enhancement, H1299 and H460 cells were seeded in 6-well plates ($2\times10^5$ cells/2 mls/well). After an overnight incubation period (37° C., 5% $CO_2$), the initial medium was replaced with freshly prepared media (2 ml) containing 0.062 μg/ml CDDP (Sigma Chemicals, St. Louis, Mo.) (CDDP was prepared fresh by dissolving in distilled water) and the cells were then incubated for 24 hours at 37° C., with 5% $CO_2$. CDDP-treated cells were then washed twice with PBS and subsequently infected with Ad/CMV/β-gal (MOI=1 for H1299 and MOI=5 for H460) on days 0, 1, 2, 3, 4, 5 or 6 following CDDP removal, to determine the time point at which maximal enhancement of expression was occurring. To establish the dose of CDDP needed to produce maximum enhancement, the cells were treated with different concentrations of CDDP (serial, 1:4 dilutions, ranging from 4 μg/ml to 0.0002 μg/ml, 5 ml per 60 mm dish) for 24 hours and subsequently incubated with Ad/CMV/β-gal 48 hours after removal of CDDP. To study if exposure of malignant cells to different classes of antineoplastic agents would lead to a similar elevation of gene expression, H1299 cells were treated with vincristine (Eli Lilly and Co, Indianapolis, Ind.), methotrexate (Lederle Pharmaceuticals, Pearl River, N.Y.), 5-fluorouracil (SoloPak Laboratories, Elk Grove Village, Ill.), epotoside (Bristol Laboratories, Princeton, N.J.) and transplatin (the isomer of CDDP that has no anticancer activity, Sigma Chemical, St. Louis, Mo.) in the similar fashion as CDDP treatment and then infected with Ad/CMV/β-gal 48 hours after removal of drug-containing media. H1299 cells were treated with 2, 4, 8, or 16 Grey (Gy) of ionizing irradiation and then similarly infected 72 hours after irradiation. Untreated cells that were similarly infected, served as controls.

Gene Transfer Vectors: The recombinant adenovirus carrying the *Escherichia coli* β-*galactosidase* gene under the control of the human cytomegalovirus enhancer/promotor (Ad/CMV/β-gal) or the replication defective adenovirus were propagated on 293 cells and purified and stored using techniques previously reported (Nguyen et al., 1996). Viral titer was determined by UV spectrophotometric analysis (Nguyen et al., 1996a; 1996b). To determine if the CDDP-induced enhancement of gene expression would be dependent on the method of gene delivery, two other gene delivery systems were used: the Ad/PLL/DNA complex (Nguyen et al., 1996a; 1996b) and cationic liposomes (Lipofectamine, Gibco BRL). CDDP (0.062 μg/ml)-treated H1299 cells were incubated with either gene delivery system carrying a plasmid that contained the β-gal gene under the control of the CMV enhancer/promotor (CMV/β-gal) 48 hours after drug removal. Plasmid DNA was isolated by the alkaline lysis technique and purified by using Qiagen DNA purification kits (Qiagen, Chatsworth, Calif.). Plasmid containing liposome preparations and gene transfer were performed according to the manufacturer's protocol. The conjugated Ad/PLL/DNA complex was constructed and used to deliver the β-gal gene to H1299 and H460 cells as described elsewhere (Nguyen et al., 1996a; 1996b).

Quantitation of β-gal Gene Expression: Adenoviral infection was performed 2 days after exposure to CDDP (0.062 μg/ml×24 hours), with cell extracts being obtained 24 hours later and quantitatively assayed for the expression of the β-galactosidase gene using O-nitrophenyl β-d-galactoside (ONPG) as a substrate (MacGregor et al., 1987). The magnitude of CDDP-induced enhancement of gene expression at a given MOI was determined by calculating the enhancement index:

$$\text{Enhancement index} = \frac{\beta\text{-gal activity of } CDDP\text{-treated cells}}{\beta\text{-gal activity of control cells}}$$

In Vivo CDDP-Induced Enhancement of β-gal Gene Expression

Subcutaneous (SC) tumor nodules were created by injecting $1\times10^7$ H1299 cells suspended in 100 μl of PBS into the dorsal flank SC tissue of nude mice (nu/nu, Charles River, Wilmington, Mass.) that had received 350 Rads of total body irradiation. Tumors, approximately 250 mm³ in size, consistently formed within 3 to 4 weeks of tumor cell implantation. Intratumoral injections of Ad/CMV/β-gal ($5\times10^8$ viral particles) were done at 0, 2, 4, and 6 days following an intraperitoneal injection of CDDP (5 μg/g body weight in 100 μl of PBS) or PBS only (n=4 per groups). The tumors were excised 48 hours after adenovirus injection, washed in cold PBS, embedded in tissue freezing medium (Fisher Scientific, Houston, Tex.) and snap-frozen by immersion in 2-methylbutane which was chilled over liquid nitrogen. Serial frozen sections (8 μl, thick) of the tumor mass obtained at 2-mm intervals were fixed and stained with X-gal as previously described (Ponder et al., 1991) and then counterstained with nuclear fast red (PolyScientific, Bay Shore, N.Y.). Quantitative assessment of β-gal gene expression (blue cells) was determined by digital image analysis (Samba 4000, Immuno Software, Version 3.0; Image Products International, Inc., Chantilly, Va.) for each tumor section. In vivo β-gal gene transduction of tumor masses was calculated as the mean of the percentage of blue cells per surface area of representative sections. Tumor-bearing animals receiving intraperitoneal injection of PBS and subsequent intratumoral injection of Ad/CMV/β-gal at identical time points, served as controls. The magnitude of enhancement was calculated by dividing values from CDDP and Ad/CMV/β-gal treated tumors by values from Ad/CMV/β-gal control treated tumors.

Statistical Analysis

The results are presented as means±standard deviations. Analysis of variance (ANOVA) and Student's t-test were used for statistical analysis; p<0.05 is considered significant.

RESULTS

Time Course and Dose Response Analysis

Figure 1B:
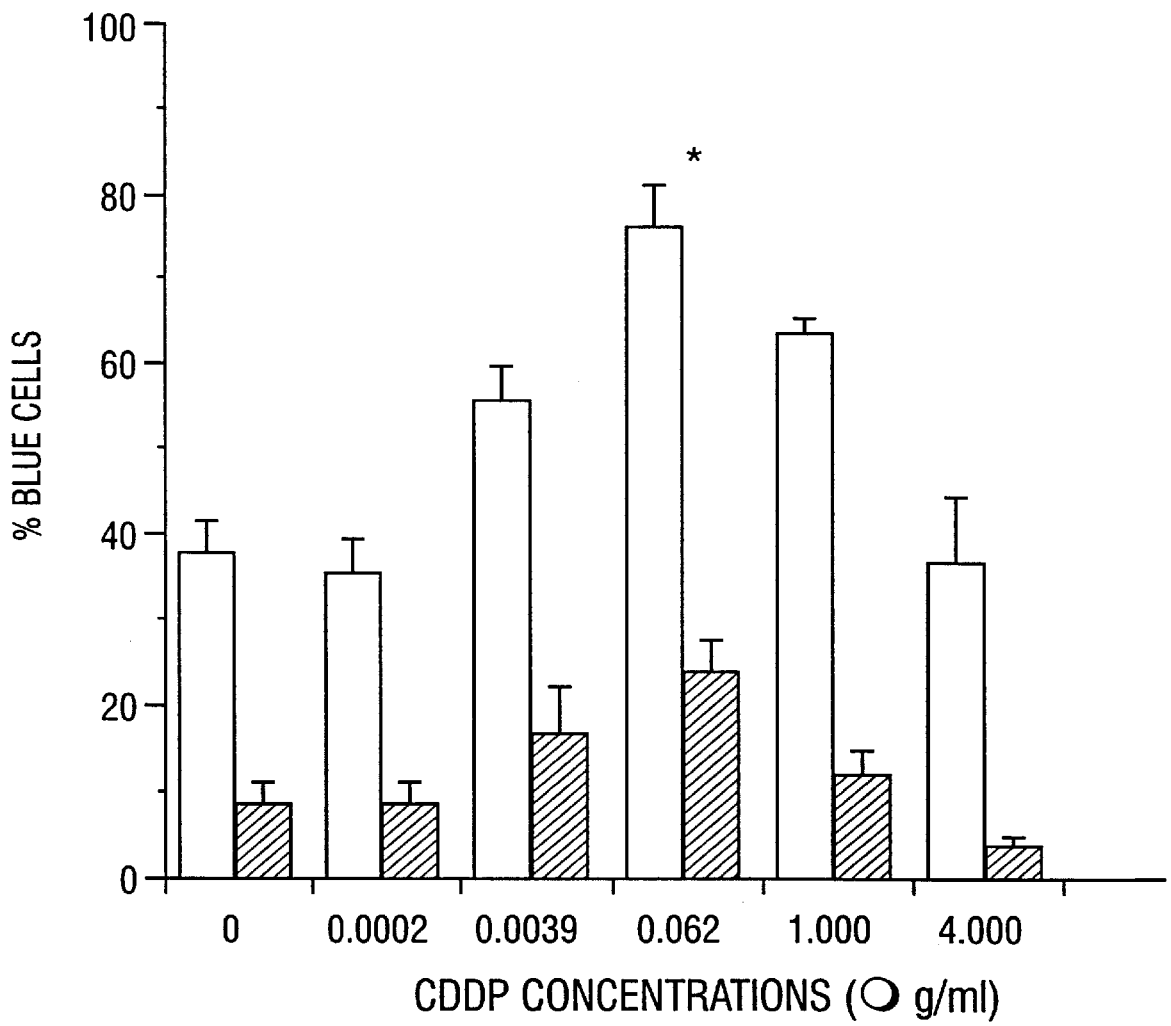
FIG. 1B—Dose Response Analysis of CDDP Treatment. Dose response curve of CDDP-induced enhancement of β-gal gene expression in H1299 (open bar) and H460 (hatched bar) cells. Maximal enhancement of β-gal gene expression was observed in cells exposed to 0.062 μg/ml×24 hrs (*=p<0.001 by ANOVA and Student's t test); mean±SD (n=6; results of two experiments with triplicate samples). Cells were stained for β-gal expression, 24 hrs after infection.

The initial response of incubating the H1299 and H460 cells with CDDP at 1 and 4 μg/ml for 24 hours, ranged from a significant depression of growth to complete inhibition of proliferation, however, those cells were viable as demonstrated by trypan blue exclusion. At CDDP concentrations lower than 0.25 μg/ml, cell growth remained unchanged as compared to control cells populations. A brief 24-hour exposure of H1299 and H460 cells to CDDP (0.062 μg/ml) resulted in an increase of gene expression in target cells infected by Adv/CMV/β-gal as quantitated by X-gal staining (FIG. 1A). Maximal enhancement (2 to 2.5 fold increase in the percentage of positively stained cells as compared to concurrent controls) was noted when cells were infected with Adv/CMV/β-gal 48 hours after removal of CDDP (p<0.001). The enhancement effect was short-lived as the percentage of positively stained, treated cells, infected on day 4 or 5 after CDDP exposure was similar to that of the control. There was also a clear CDDP dose-related enhancement of β-gal gene expression in H1299 and H460 cells when infected with Adv/CMV/β-gal 48 hours after CDDP removal (FIG. 1B). Maximal enhancement occurred at a CDDP concentration of 0.062 μg/ml, however, there was also an enhancement at 0.0039 and 1 μg/ml. Optimal conditions for maximal enhancement of gene expression thus appears to be at the CDDP concentration of 0.062 μg/ml and gene transfer at about 48 hours after drug treatment.

Mechanism of Enhanced Gene Expression

Figure 2A:
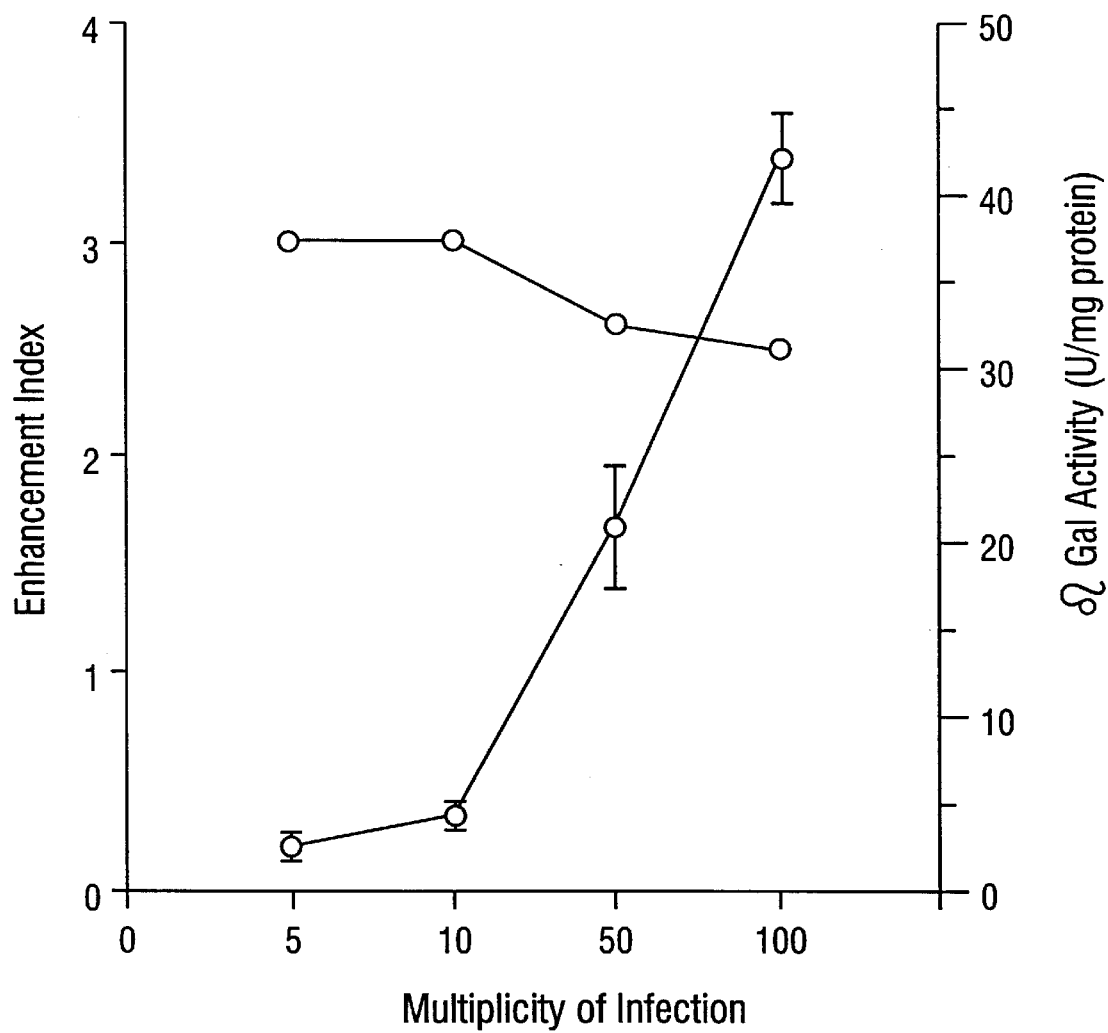
FIG. 2A—Enhancment of β-gal Gene Expression in CDDP-Treated Cells in Relation to Increasing MOI's. The β-gal activity of CDDP-treated H1299 cells was quantitated by the ONPG assay, 24 hrs after incubation with Ad/CMV/β-gal. Open circles represent enhancement index; filled circles represent β-gal activity; mean±(n=4; results of two experiments with duplicate samples).
Figure 2B:
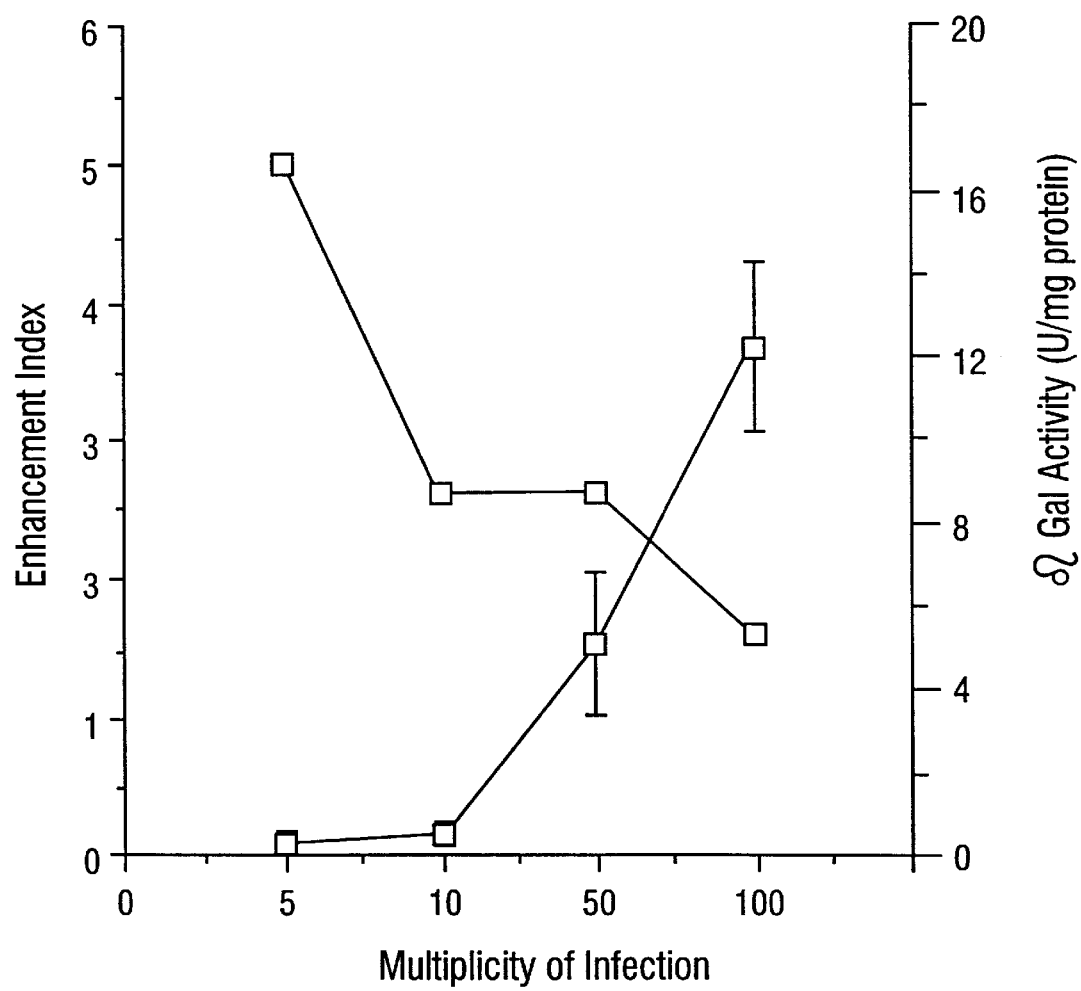
FIG. 2B—Enhancement of β-gal Gene Expression in CDDP-Treated Cells in Relation to Increasing MOI's. The β-gal activity of CDDP-treated H460 cells was quantitated by the ONPG assay, 24 hrs after incubation with Ad/CMV/β-gal. Open circles represent enhancement index; filled circles represent β-gal activity; mean±(n=4; results of two experiments with duplicate samples).

To determine if prior incubation of target cells with CDDP would result in an increase in the ability of cells to take up gene-delivering vectors or an increase in the expression of successfully delivered genes, β-gal gene expression was quantitated in H1299 and H460 cell lines treated with CDDP and then infected with Ad/CMV/β-gal at increasing MOI's. If CDDP mediates an enhancement of adenovirus uptake as compared to non-treated controls, then there should be a proportional increase in enhancement indices with increasing MOI's. On the other hand, if prior CDDP exposure results in enhanced gene expression only, then the enhancement index should be independent of the increasing MOI. The analysis showed that the β-gal activity in H1299 infected cells increased as the MOI's were elevated from 5 to 100 (control H1299 cells of 0.82±0.11 to 16.8±3.2 U/mg protein and CDDP-treated H1299 cells of 2.2±0.40 to 42.0±2.6 U/mg protein), indicating unchanged enhancement indices (3 to 2.5) with increasing MOI's (FIG. 2A). Similarly, β-gal gene expression in CDDP-treated H460 cells increased from 0.28±0.06 to 12.2±2.1 U/mg protein, as compared to β-gal gene expression in control H460 cells of 0.056±0.016 to 7.6±1.8 U/mg protein. The enhancement indices in H460 cells, therefore, decreased from a value of 5 at an MOI of 5, to a value of 1.6 at an MOI of 100 (FIG. 2B). This observation implies that CDDP induces an increase in the expression of successfully delivered genes and not an increase in adenovirus uptake.

Enhanced β-gal Gene Expression by DNA-Damaging Agents

Figure 3:
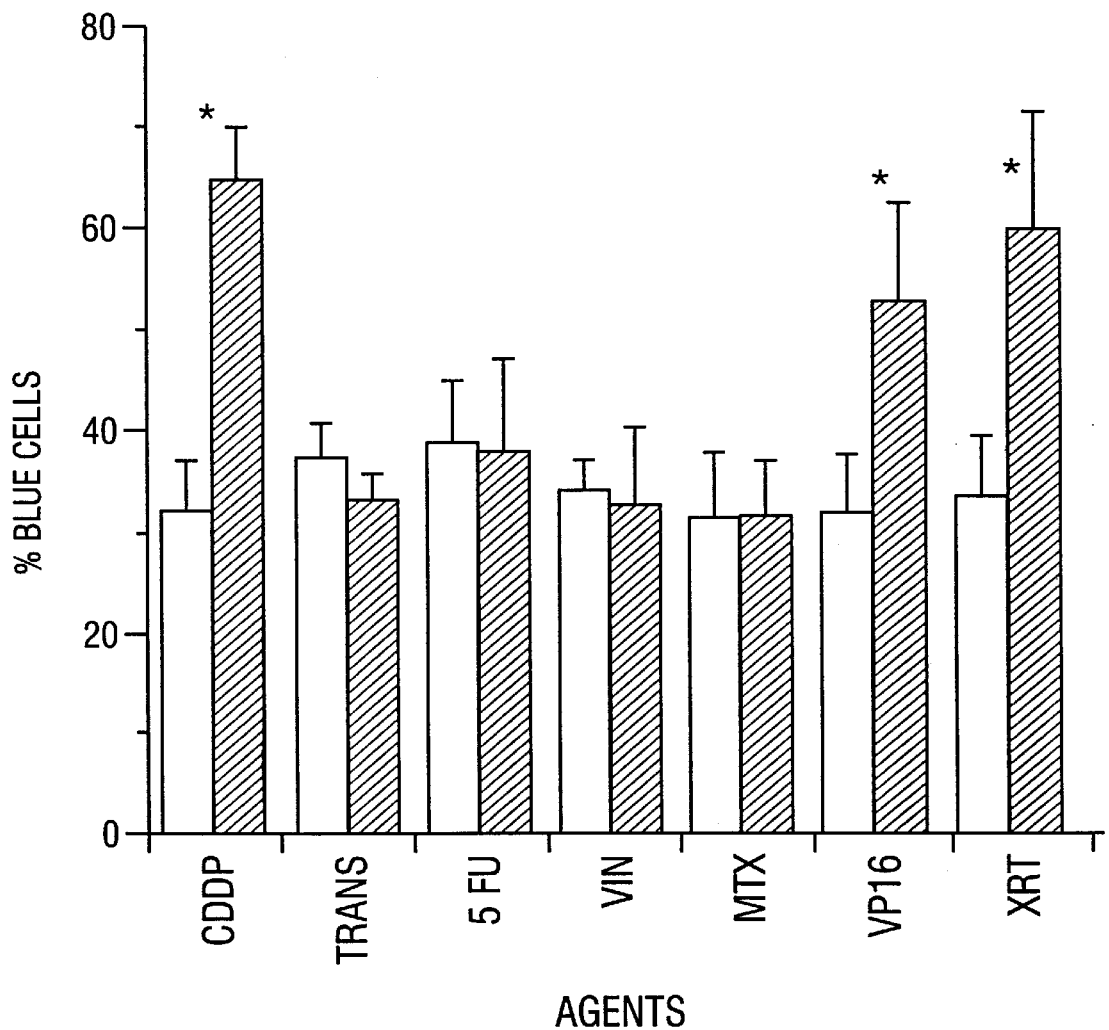
FIG. 3—Enhancement of β-gal Gene Expression Following Exposure to DNA-Damaging Agents. Enhancement of β-gal expression was observed following treatment with DNA-damaging agents (CDDP, Etoposid (VP16) or ionizing radiation (XRT)), but not to other anti-neoplastic agents (Methotrexate (MIX), Vincristine (VIN), 5-Fluorouracil (5FU) or Transplatinum (TRANS)). Only data of cells treated with drugs (hatched bar) at the concentration of 0.062 μg/ml or irradiated with 8 Greys are shown here along with data of non-treated cells (open bar); mean±SD (n=6; results of two experiments with triplicate samples). Cells were stained for β-gal expression, 24 hrs after infection (*=p<0.001 by ANOVA and students t test).

Infection of H1299 cells that were similarly treated with other antineoplastic agents such as vincristine, methotrexate, 5-fluorouracil or trnsplatinum with Ad/CMV/β-gal did not result in enhanced gene expression over a wide range of drug concentrations (FIG. 3). Methotrexate and 5-FU are antimetabolites which interfere with synthesis of nucleic acid precursors; vincristine binds to and inhibits microtubular formation and impairs cellular mitosis (Fritsch et al., 1993). On the other hand, exposure of H1299 cells to the DNA-damaging agents VP-16 (etoposide) and ionizing irradiation (at 4 and 8 Grey) enhanced gene expression in tumor cells infected with Adv/CMV/β-gal (FIG. 3). These pharmacological agents induce DNA strand breaks by different mechanisms: CDDP causes intra- and inter-strand crosslinking of DNA by forming guanine adducts and eventually DNA strand breaks (Eastman, 1990); Etoposide forms a tertiary complex between DNA and topoisomerase II and eventually produces protein-linked DNA single and double strand breaks (Kaufman, 1989); ionizing irradiation stimulates production of oxygen free radicals which react with macromolecules and induces DNA damage (Cole et al., 1980).

Enhanced β-gal Gene Expression in Other Cell Types and With Different Vectors

Figure 4A:
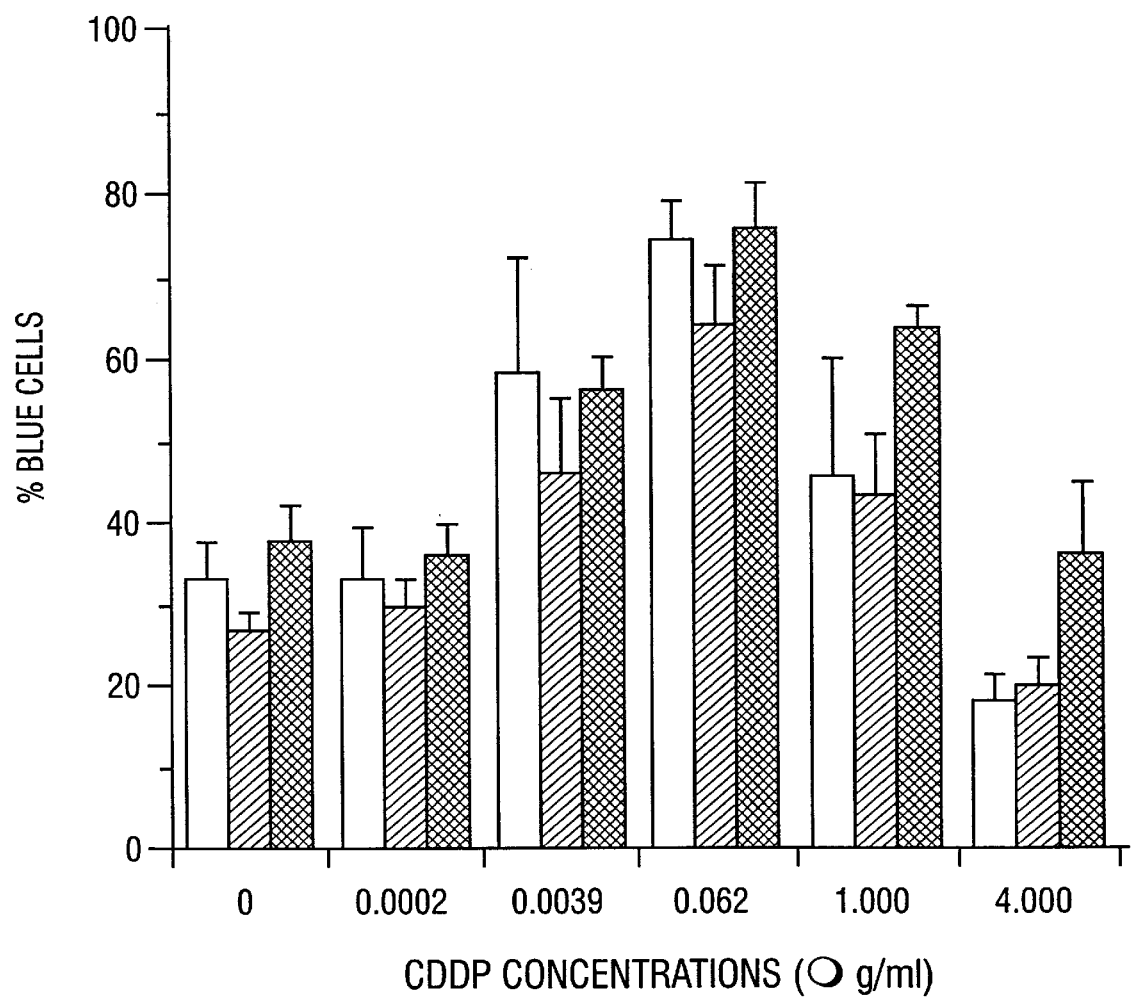
FIG. 4A—Effect of CDDP on Reporter Gene Expression Using Different Vectors. Ad/CMV/β-gal (open bar), Ad/PLL/DNA complex (hatched bar) or lipofectamine (solid bar) carrying a β-gal expressing plasmid were incubated with CDDP-treated (0.062 μg/ml for 24 hrs) H1299 cells 48 hrs after CDDP removal; mean±SD (n=6; results of two experiments, with triplicate samples) (*=p<0.001 by ANOVA and Student's t test). Cells were stained for β-gal expression, 24 hrs after vector administration.
Figure 4B:
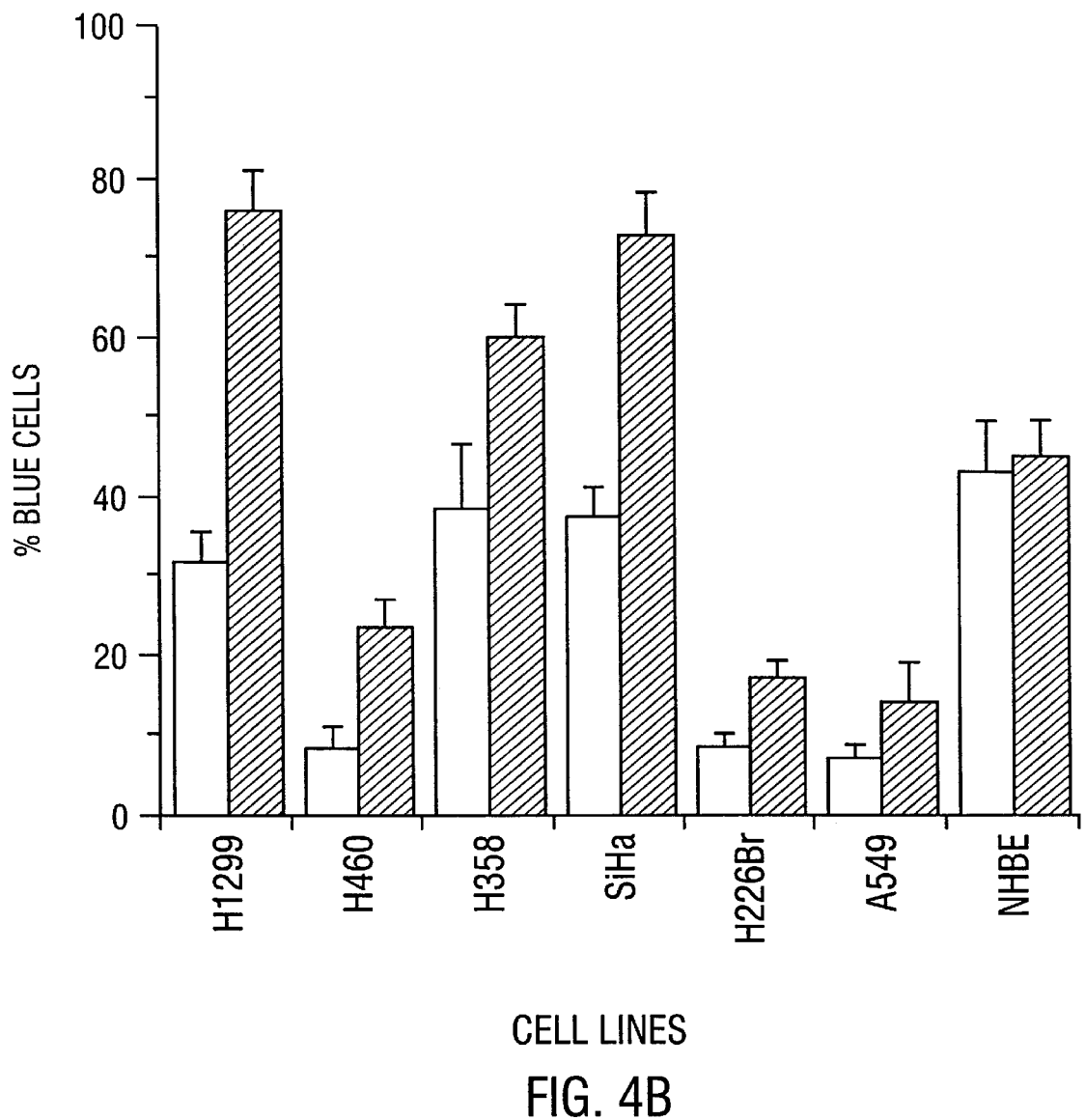
FIG. 4B—Effect of CDDP on Reporter Gene Expression Using Different Cell Types. Ad/CMV/β-gal was used to infect malignant and normal cells that were CDDP-treated (hatched bar) or untreated (open bar) with Ad/CMV/β-gal. Infection was performed on day 2 following exposure to CDDP (0.062 μg/ml for 24 hrs) or mock exposure with PBS. Only data of cells treated with 0.062 μg/ml CDDP are shown. MOI=1 (H1299; SiHa); MOI=5 (H460, NHBE); MOI=10 (H358, H226br, A549). Mean±SD (n=6; results of two experiments, with triplicate samples). Cells were stained for β-gal expression, 24 hrs after infection.

When CDDP-treated H1299 cells were incubated with 2 other gene delivery systems (the conjugated Ad/PLL/DNA complex or the cationic phospholipid lipofectamine), β-gal gene expressing cells occurred at the same CDDP doses and to the same magnitude as observed following adenovirus-mediated gene transfer (FIG. 4A). This indicates that the enhancement by CDDP is not vector dependent. This CDDP-induced enhancement of transgene expression following Ad/CMV/β-gal infection was also observed in other malignant cell lines tested under the same experimental conditions (FIG. 4B). The magnitude of maximal enhancement was dependent on the cell line tested (ranging from 1.6-fold (A549) to 2.7-fold (H1299)), but it consistently occurred when gene transfer was performed 48 hours after exposure to 0.062 μg/ml of CDDP. Similar exposure of stationary primary human bronchial epithelial cells (90% confluent in culture) to a low concentration (0.062 μg/ml) of CDDP failed to enhance gene expression in these normal cells after Ad/CMV/β-gal infection (FIG. 4B). However, at higher drug concentrations (1 and 4 μg/ml), there was a dose-dependent elevation of the percentage of β-gal-positive cells that was 1.5- to 2.5-fold higher than that observed in unexposed NHBE cells.

In Vivo Enhancement of β-gal Gene Expression

Figure 5:
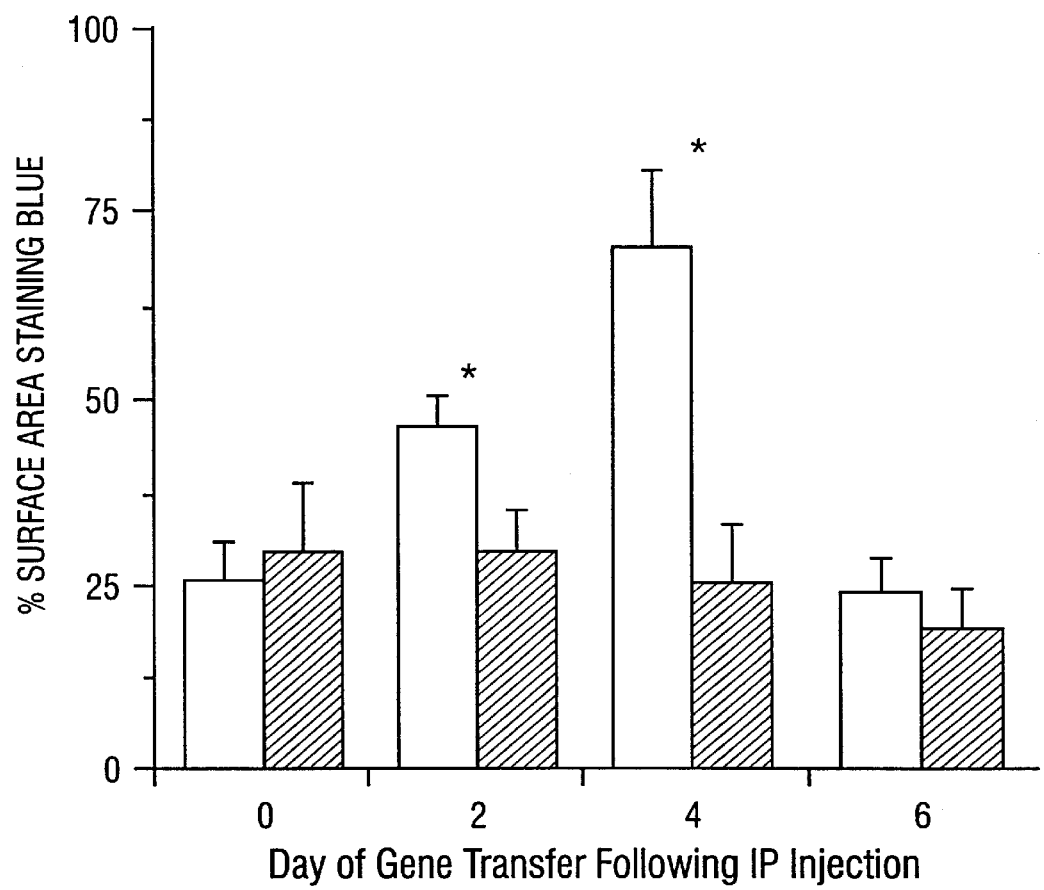
FIG. 5—In Vivo Enhancement of β-gal Expression by Sequential Administration of CDDP and Intratumoral Injection of Ad/CMV/β-gal. In vivo enhancement of β-gal expression by sequential administration of CDDP (5 μg/g body weight; intraperitoneal injection) and intratumoral injection of Ad/CMV/β-gal ($5 \times 10^8$ viral particles) on the same day (day 0), 2, 4 or 6 days after CDDP administration; mean±(n=4 animals) (*=p<0.001 by ANOVA and Student's t test). Open bar=CDDP treated animals; hatched bar=PBS treated animals. β-gal analysis was done 24 hrs after vector administration.

To analyze the effect of CDDP on enhancing gene expression in tumor cells in vivo, a time course analysis was done. The time course of enhanced β-gal expression in H1299 cells in vivo was similar to the in vitro time course (FIG. 5). The overall gene expression in subcutaneous H1299 tumors of animals injected with PBS and Ad/CMV/β-gal slightly decreased (29.2±9.0% on day 0 to 18.2±5.6% on day 6) over time as tumors continued to grow while the viral titer remained unchanged. There was no change in the β-gal gene expression in H1299 cells when CDDP and Ad/CMV/β-gal were concurrently administered (day 0). However, the percentages of positively stained cells in tumors injected with Ad/CMV/β-gal 2 and 4 days after CDDP administration were 1.6- to 2.8-fold higher than the values of the respective controls (46.0±4.3 vs 28.7±6.2 on day 2 and 70.2±11 vs. 25.0±7.0 on day 4, p<0.01). When gene transfer was performed 6 days after CDDP administration, the increase in expression was slightly higher than that of the control tumors (23.4±5 vs. 182.0±5.6, p (FIG. 5).

EXAMPLE 2: GENE THERAPY STRATEGY FOR HUMAN NON-SMALL CELL LUNG CANCER: COMBINATION OF SEQUENTIAL CISPLATIN ADMINISTRATION AND ADENOVIRUS-MEDIATED p53 GENE TRANSFER

Materials and Methods

Cells and Culture Conditions

The human NSCLC cell line H1299 with a homozygous deletion of p53 gene was grown in RPMI-1640 medium supplemented with 5% heat-inactivated fetal calf serum (FCS), 10 mM glutamine, 100 units/ml of penicillin, 100 µg/ml of streptomycin, 0.25 µg/ml of amphotericin B (Gibco-BRL, Grand Island, N.Y.) (RPMI-complete). The H322 cell line was maintained in RPMI-complete medium supplemented with 10% FCS. The 293 cells were maintained in complete high glucose Dulbecco's modified Eagle's medium (DMEM) supplemented with 10% heat-inactivated FCS.

Recombinant Adenovirus Production

The properties of the adenovirus Ad/CMV/p53 have previously been demonstrated in the inventors' laboratory (Diller et al., 1990). The replication-defective E1A-deleted adenovirus d1312 was used as a control. The virus was amplified on a large scale on 293 cells according to methods previously reported (Zhang et al., 1995a). Viral titer was determined by UV-spectrophotometric analysis (viral particles/ml). The absence of replicative competence adenovirus was verified by a PCR™ technique previously reported by Zhang et al. (1995b). The purified virus was stored in 10% glycerol at −80° C. Infection of H1299 cells was carried out by dilution of the viral stock to appropriate concentrations, followed by the addition of viral solutions to cell monolayers incubated in 1 ml of RPMI-1640 medium containing 2% FCS. The cells were incubated for 2 hrs at 37° C. in a 5% $CO_2$ incubator, after which 2 ml of RPMI-1640 complete medium supplemented with 5% FCS was added into the wells.

Cell Proliferation Assay

H1299 cells were exposed to CDDP (0.062 µg/ml of medium) for 24 hrs. Cells were then washed twice with PBS, trypsinized and seeded in 6-well plates ($10^5$ cells/well). Forty eight hours later, cells were infected with Ad/CMV/p53 at the multiplicity of infection (MOI) of 5. Daily cell counts were performed for 5 days following transfection to study the tumor suppression effect of the combination of sequential CDDP and adenovirus-mediated p53 gene transfer. Controls consisted of untreated cells or cells exposed to CDDP only, cells transfected with Ad/CMV/p53 only and cells transfected with d1312 (similar MOI) with or without prior CDDP treatment.

Western Blot Analysis

H1299 cells were infected with Ad/CMV/p53 (MOI=1) 48 hrs after CDDP exposure. Cells were then harvested at 6, 12, 24, 36 and 48 hrs after transfection for Western blot analysis of p53 protein expression, as described elsewhere (Diller et al., 1990). Unexposed cells similarly transfected with Ad/CMV/p53 were used as controls. The human NSCLC cell line H322 which overexpresses mutant p53 protein was used as a positive control. Relative quantities of exogenous p53 protein were determined by densitometer (Molecular Dynamics, Sunnyvale, Calif.).

p53 Immunocytochemical Staining

The infected cells were fixed 3.8% formalin at 12 and 24 hrs after transfection with Adv/CMV/p53 (MOI=5) with or without prior CDDP exposure and treated with 3% $H_2O_2$ in methanol for 5 minutes. The Vectastain kit (Vector Laboratories, Burlingana, Calif.) was used for the immunocytochemical staining. The primary antibody used was the mouse monoclonal anti-p53 antibody Pab 1801 (Oncogene Science, Manhasset, N.Y.). The secondary antibody was the biotinylated anti-mouse IgG antibody (Vector Laboratories). The avidin-biotin-peroxidase complex (ABC) kit was used to detect the antigen-antibody complex. The cells were counterstained with Harris Hematoxylin (Sigma, St. Louis, Mo.) and mounted with cover slips using Cytoseal 60.

In Situ TUNEL Assay for Apoptosis

CDDP-treated or control H1299 cells were fixed in 50% acetone/ethanol for 20 minutes at −20° C. 12 hrs and 24 hrs after transfection with Adv/CMV/p53 (MOI=5). In situ TdT (terminal deoxynucleotidyl transferase)-mediated dUTP-biotin nick end-labeling (TUNEL) assay was performed according to the procedure described elsewhere (Gavrieli et al., 1992). H1299 cells used as positive controls were treated with DNAse I (Gibco BRL, Gaithersburg, Md.), for 1 hr at 37° C. (50 µg/ml in 10 mM Tris-HCl pH=7.5; 140 mM sodium cacodylate, 4 mM $MgCl_2$, 10 mM dithiothreitol).

In Vivo Combination of Sequential CDDP and Adv/CMV/p53 Administrations

H1299 tumor xenografts were created by injecting $1\times10^7$ cells suspended in 100 µl of PBS into the dorsal flank subcutaneous space of nude mice that had received 350 Rads of total body irradiation prior to injection. Subcutaneous tumor nodules of 200 to 250 $mm^3$ in size were formed 3 to 4 weeks later. Different strategies of CDDP and Ad/CMV/p53 combination were studied for their tumoricidal efficacy: a) intraperitoneal (ip) CDDP (5 µg/g body weight) given on day 0 and followed by intratumoral Ad/CMV/p53 injections of $1.5\times10^{10}$ viral particles/100 µl PBS in a single dose on day 3 or in 3 equally divided doses of $5\times10^9$ viral particles/100 µl PBS on days 2, 4 and 6; b) simultaneous CDDP and Ad/CMV/p53 administrations in single or 3 equally divided doses (divided CDDP doses: 1.67 µg/g body weight) and c) ip CDDP given 3 days after completion of intratumoral Ad/CMV/p53 injections. The divided dose regime was designed to address issues that may limit the use of high virus titer and volume of injectate such as toxicity and the low titer of viral stock. The controls consisted of tumors injected with either PBS, Ad/CMV/p53 without prior systemic CDDP, d1312 with or without prior ip CDDP or tumor-bearing animals receiving ip CDDP only. Tumor sizes were measured every 2 days for 32 days and tumor volumes were estimated by assuming a spherical shape with the average tumor diameter calculated as the square root of the product of the orthogonal diameters. All animals were treated according to guidelines developed by the M. D. Anderson Animal Care and Use Committee. All mice were sacrificed when tumors grew to 4000 $mm^3$.

Statistical Analysis

Results were presented as mean±standard deviation. Analysis of variance (ANOVA) and two-tailed Student's t test were used for statistical analysis of multiple groups and pair-wise comparison respectively, $p<0.05$ is considered significant.

RESULTS

In Vitro Proliferation Assay

Figure 6:
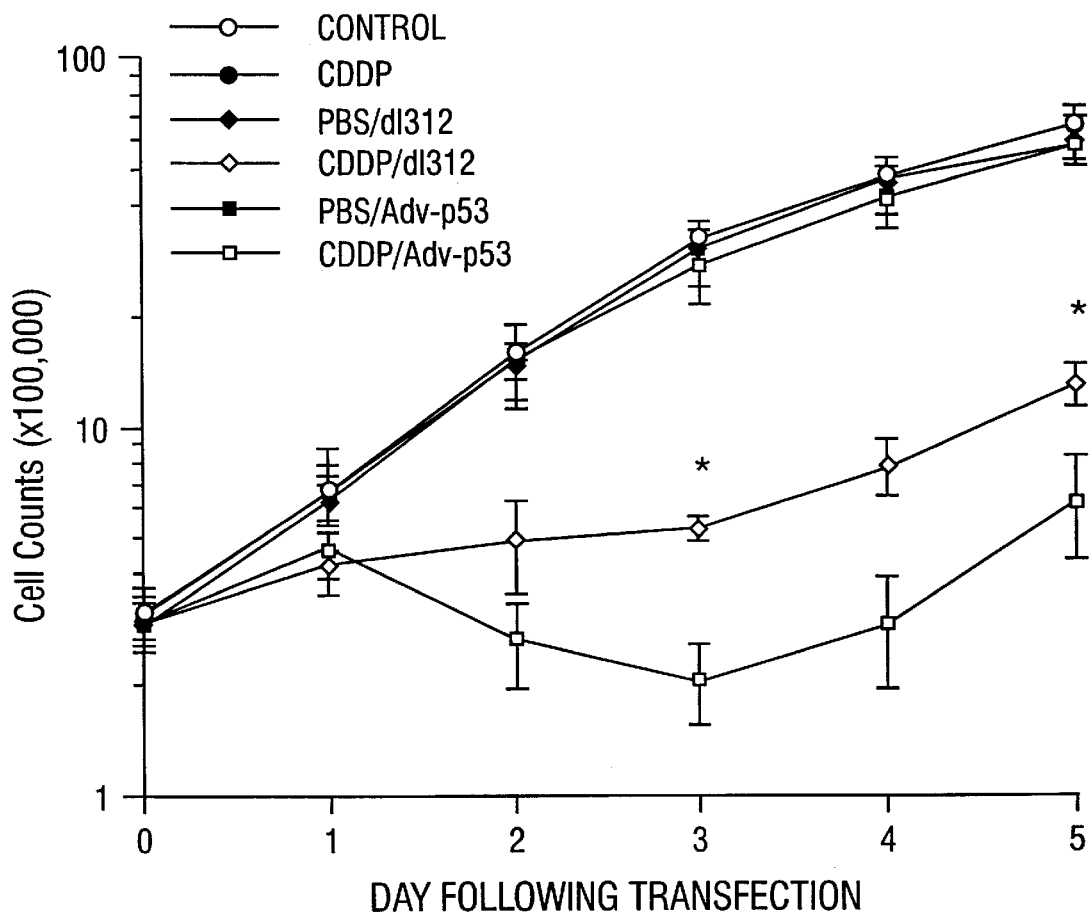
FIG. 6—Enhancement of tumor killing effect by the combination of CDDP and Ad/CMV/p53 in vitro. Cells were exposed with CDDP (0.062 μg/ml) for 24 hrs, then transfected with either Ad/CMV/p53 or dl312 (MOI=5) 2 days later. Unexposed cells served as controls; *=p<0.001 by Student's t test, n=5.
Figure 7A:
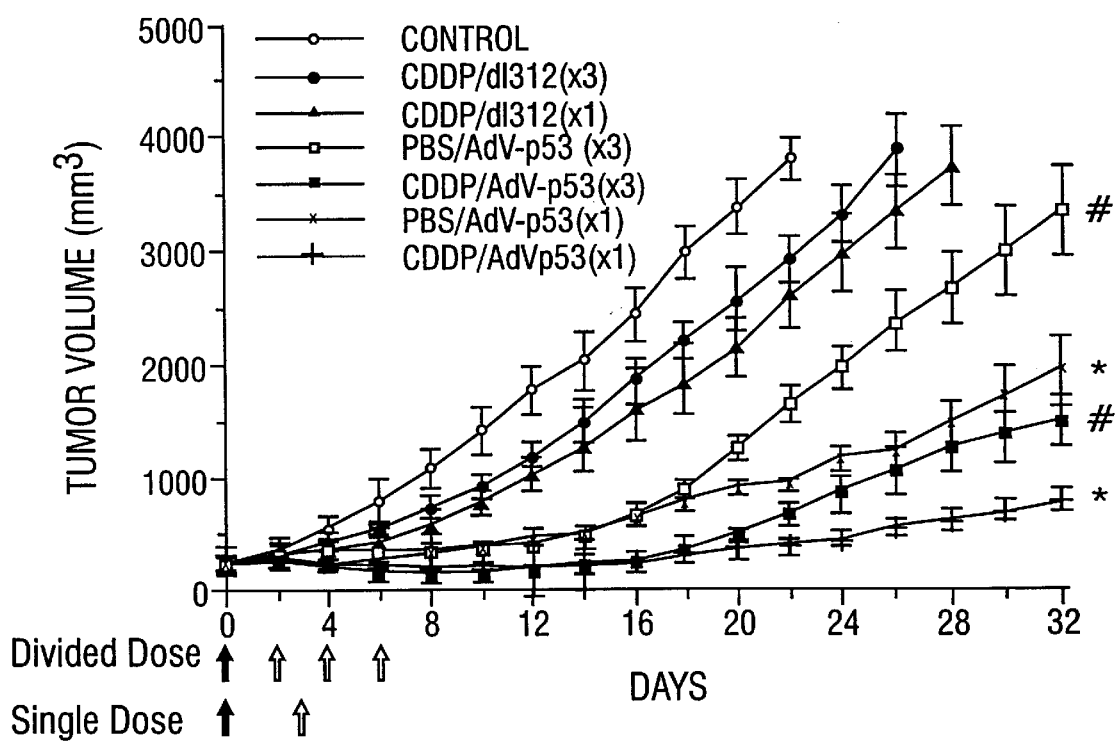
FIG. 7A—Superior in vivo tumor suppression of sequential intraperitoneal CDDP and intratumoral Ad/CMV/p53 administrations. A divided dose regimen ($1.5 \times 10^{10}$ viral particles in three equal doses injected on alternate days) for the administration of CDDP (solid arrow) and Ad/CMV/p53 (open arrow), or a single dose regimen ($1.5 \times 10^{10}$ viral particles in a single dose) with or without CDDP is shown (p<0.001 by Student's t test).
Figure 7B:
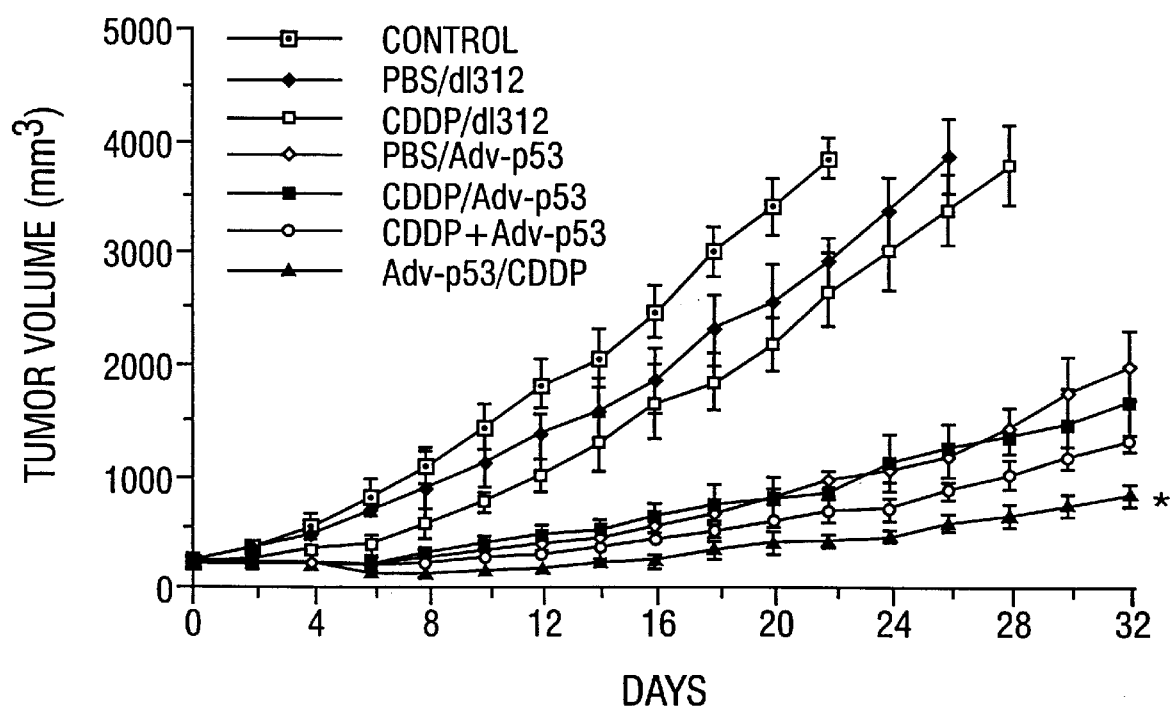
FIG. 7B—Superior in vivo tumor suppression of sequential intraperitoneal CDDP and intratumoral Ad/CMV/p53 administrations. A single dose regimen with CDDP given either before (CDDP on day 0, Ad/CMV/p53 on day 3), concurrent with (CDDP+Ad/CMV/p53 on day 0) or after (Ad/CMV/p53 on day 0, CDDP on day 3) is shown (p<0.001 by ANOVA and Student's t test; n=5 per group).

H1299 cells were treated with a combination of sequential CDDP and Ad/CMV/p53 infection and then analyzed by cell proliferation assay to determine if the combination of CDDP and adenovirus-mediated p53 gene transfer would result in a superior growth-inhibiting effect. Treating H1299 cells with CDDP (0.0625 µg/ml) for 24 hrs had no effect on cell growth in vitro, nor did mock infection with d1312 with or without prior CDDP treatment. On the other hand, exposure of H1299 cells to CDDP 48 hrs prior to Adv/CMV/p53 transfection resulted in 61% and 55% increased inhibition of tumor proliferation on day 3 and 5 after p53 transfer when compared to control H1299 cells similarly transfected with Adv/CMV/p53 (FIG. 6).

Western Blot Analysis and p53 Immunocytochemical Staining

The effect of CDDP treatment on levels of p53 protein was determined in CDDP-treated and untreated control cells by Western blotting of cell lysates harvested at different time points after Adv/CMV/p53 infection. Expression of the p53 gene occurred as early as 6 hours after Adv/CMV/p53 transfection in both CDDP-treated and control H299 cells. However, prior exposure to CDDP led to a higher level of p53 at 12, 24, 36 and 48 hrs after transfection. Densitometry analysis showed that the relative levels of p53 protein (normalized for $\beta$-actin levels) in CDDP-treated cells were 0.73, 1.39, 1.49. 1.20 compared to 0.23, 0.90, 0.68, 0.62 (for a 2- to 3-fold increase in the levels of p53 protein) in cells without prior CDDP at each of the time points studied. The p53 levels at 6 hrs after transfection were too low to be analyzed. CDDP treatment appeared to significantly increase the p53 gene expression but did not seem to alter the transduction kinetics of H1299 cells. Immunocytochemical staining of H1299 cells 24 hrs after p53 gene transfer demonstrated that almost all of the CDDP-treated cells stained positive, at a significantly higher intensity, for the p53 protein as compared to cells not exposed to CDDP. This elevation of p53 gene expression correlates well with the enhanced tumoricidal effect of the combination of CDDP and Adv/CMV/p53 in vitro as demonstrated in FIG. 6.

Induction of Apoptosis Following Adv/CMV/p53 Transfection

The in situ TUNEL assay was used to analyze the extent of apoptosis that occurred in Ad/CMV/p53-transfected H1299 cells. In cells that were not exposed to CDDP prior to gene transfer, apoptosis began 12 hrs after p53 transfection with few TUNEL-positive cells being visualized with significant apoptosis was detected 24 hrs after Ad/CMV/p53 transfection. Apoptotic cells could be readily seen in CDDP-treated cells as early as 12 hrs after transfection, at a much higher frequency than in untreated cells. By 24 hrs, almost all CDDP-treated cells stained positive for DNA fragmentation. The degree of apoptosis and the timing of its occurrence follow very closely the time course of p53 gene expression in CDDP-treated cells. Thus enhanced and accelerated p53 gene expression in cells treated with sequential CDDP and Ad/CMV/p53 most probably resulted in an early and intense induction of apoptosis which translated to an increased tumoricidal effect.

Inhibition of Tumor Growth In Vivo

Divided-Dose Regime: Tumors grew rapidly in groups of control animals receiving only ip CDDP or intratumoral PBS with tumor sizes reaching the maximal allowable volume of 4000 mm$^3$22 to 26 days after treatment. Tumors injected with d1312 with or without prior ip CDDP showed some degree of growth retardation (up to 30% of normal tumor growth) secondary to vector toxicity. Injections of Ad/CMV/p53 ($1.5 \times 10^{10}$ viral particles in 3 equally divided doses) resulted in inhibition of tumor growth during and immediately after the treatment. These tumors, however, resumed growth at the normal rate, 10 days after the last injection; reaching the mean tumor volume of 3357±391 mm$^3$32 days after the onset of therapy. Intraperitoneal CDDP administration given 2 days prior to the beginning of the gene therapy schedule resulted in a more pronounced inhibition of tumor development. There was a regression of tumor mass that lasted for 14 days before the tumor growth resumed which was at a much slower rate. At the end of the observation period, the average tumor size was 1497±221 mm$^3$ ($p<0.001$vs Ad/CMV/p53 without prior CDDP). Systemic CDDP administration prior to p53 gene replacement therapy, therefore, resulted in a synergistic effect of tumor growth inhibition that was responsible for at least a 55.4% further reduction in tumor size.

Single-Dose Regime: When Ad/CMV/p53 was given in a single dose, inhibition of tumor growth was greater than that seen with the divided-dose regime: 1936±308 vs 3357±391 (without CDDP) and 773±197 vs 1497±221 (with prior CDDP) respectively. The combination of CDDP administration 3 days prior to a single intratumoral injection of Ad/CMV/p53 ($1.5 \times 10^{10}$ viral particles) resulted in a 60% further suppression of tumor growth compared to tumors treated with Ad/CMV/p53 without prior CDDP. To illustrate the importance of the timing of CDDP administration in relation to p53 gene transfer, CDDP (5 $\mu$g/ml) was given at the same time as Ad/CMV/p53 ($1.5 \times 10^{10}$ viral particles) injections in a second group of mice, and in a third group CDDP was given 3 days after adenovirus-mediated p53 gene transfer. The combination of sequential CDDP and Ad/CMV/p53 showed the most significant tumor growth inhibition effect with the mean tumor volume of 773±197 mm$^3$, compared to 1257±225 mm$^3$, when CCDP was given concurrently with adenovirus injections, and 1750±214 mm$^3$, when CDDP was given after adenovirus-mediated p53 transfer ($p<0.001$ by ANOVA). Ad/CMV/p53 significantly prolonged the survival of treated animals to 62.8±4.6 days (range: 60 to 70 days) after the onset of therapy compared to tumor-bearing mice injected with Ad/CMV/p53 alone of 46.0±4.4 days or untreated controls of 23.4±2.9 days ($p<0.001$).

H. References

The following references, to the extent that they provide exemplary procedural details or other information supplementary to that set forth herein, are incorporated by reference.

Anderson et al., U.S. Pat. No. 5,399,346.

Baichwal and Sugden, "Vectors for gene transfer derived from animal DNA viruses: Transient and stable expression of transferred genes," In: Kucherlapati R, ed. Gene transfer. New York: Plenum Press, pp. 117–148, 1986.

Bargonetti et al., *Cell*, 65:1083–1091, 1991.

Benvenisty and Neshif, "Direction introduction of genes into rats and expression of the genes," *Proc. Nat'l Acad. Sci. USA*, 83:9551–9555, 1986.

Bittner et al., *Methods in Enzymol.*, 153:516–544, 1987.

Casey et al., "Growth suppression of human breast cancer cells by the introduction of a wild-type p53 gene," *Oncogene*, 6:1791–1797, 1991.

Chang et al., "Foreign gene delivery and expreddion in hepatocytes using a hepatitis B virus vector," *Hepatology*, 14:134A, 1991.

Chen and Okayama, "High-efficiency transfection of mammalian cells by plasmid DNA," *Mol. Cell Biol.*, 7:2745–2752, 1987.

Coffin, "Retroviridae and their replication," In: Virology, Fields et al. (eds.), New York: Raven Press, pp. 1437–1500, 1990.

Colbere-Garapin et al., 1981.

Cole et al., In: Mechanisms of Injury, eds. Meyn, R. E. & Withers, H. R., 1980.

Couch et al, "Immunization with types 4 and 7 adenovirus by selective infection of the intestinal tract," *Am. Rev. Resp. Dis.*, 88:394–403, 1963.

Coupar et al., "A general method for the construction of recombinant vaccinia virus expressing multiple foreign genes," *Gene*, 68:1–10, 1988.

DeVita et al., "Cancer Principles and Practice of Oncology," 3rd. ed.

Diller et al., "p53 Functions as a Cell Cycle Control Protein in Osteosarcomas," *Mol. Cell Biol.*, 10(11):5772–5781, 1990.

Dubensky et al,. "Direct transfection of viral and plasmid DNA into the liver or spleen of mice," *Proc. Nat. Acad. Sci. USA*, 81:7529–7533, 1984.

Eastman, Cancer *Cell*, 2:275–280, 1990.

Fechheimer et al., "Transfection of mammalian cells with plasmid DNA by scrape loading and sonication loading," *Proc. Nat'l Acad. Sci. USA*, 84:8463–8467, 1987.

Ferkol et al., Ferkol et al., *FASEB J.*, 7:1081–1091, 1993.

Fields et al., *Science*, 249:1046–1049, 1990.

Fraley et al., "Entrapment of a bacterial plasmid in phospholipid vesicles: Potential for gene transfer," *Proc. Nat'l Acad. Sci. USA*, 76:3348–3352, 1979.

Freshner, "Animal Cell Culture: A Practical Approach," Second Edition, Oxford/New York, IRL Press, Oxford University Press 1992.

Friedmann, "Progress toward human gene therapy," *Science*, 244:1275–1281, 1989.

Fritsch et al., *Oncogene*, 8:307–318, 1993.

Gavrieli et al., "Identification of Programmed Cell Death In Situ Via Specific Labeling of Nuclear DNA Fragmentation," *J. Cell Biol.*, 119:493–501, 1992.

Ghosh-Choudhury, et al., "protein IX, a minor component of the human adenovirus capsid, is essential for the packaging of full length genomes," *EMBO J.*, 1733–1739, 1987.

Ghosh and Bachhawat, "Targeting of liposomes to hepatocytes," In: Wu G. and C. Wu ed. Liver diseases, targeted diagnosis and therapy using specific receptors and ligands. New York: Marcel Dekker, pp. 87–104, 1991.

Gomez-Foix et al., "Adenovirus-mediated transfer of the muscle glycogen phosphorylase gene into hepatocytes confers altered regulation of glycogen," *J. Biol. Chem.*, 267:25129–25134, 1992.

Goodman and Gilman's "The Pharmacological Basis of Therapeutics." 8th ed. Pergammon Press, New York, 1990.

Gopal, "Gene transfer method for transient gene expression, stable transfection, and cotrasfection of suspension cell cultures," *Mol. Cell Biol.*, 5:1188–1190, 1985.

Graham, et al., "Characteristics of a human cell line transformed by DNA from human adenovirus type 5," *J. Gen Virol.* 36:59–72, 1977.

Graham and Prevec, "Manipulation of adenovirus vectors." In: E. J. Murray (ed.), Methods in *Molecular Biology, Gene Transfer and Expression Protocols*, New Jersey: The Humana Press Inc., 109–128, 1991.

Graham and Van Der Eb, "A new technique for the assay of infectivity of human adenovirus 5 DNA", *Virology*, 52:456–467, 1973.

Grunhaus and Horwitz, "Adenoviruses as cloning vectors," Semin. *Virology*, 3:237–2542, 1992.

Harland and Weintraub, "Translation of mammalian MRNA injected into Xenopus oocytes is specifically inlubited by antisense RNA," *J. Cell Biol.*, 101:1094–1099, 1985.

Hennonat and Muzycska, "Use of adenoassociated virus as a mammalian DNA cloning vector: Transduction of neomycin resistance into mammalian tissue culture cells," *Proc. Nat'l Acad. Sci. USA*, 81:6466–6470, 1984.

Hersdorffer et al., "Efficient gene transfer in live mice using a unique retroviral packaging line," *DNA Cell Biol.*, 9:713–723, 1990.

Herz and Gerard, "Adenovirus-mediated transfer of low density lipoprotein receptor gene acutely accelerates cholesterol clearance in normal mice," *Proc. Nat'l Acad. Sci. USA* 90:2812–2816, 1993.

Hollstein et al., "p53 mutations in human cancers," *Science*, 253:49–53, 1991.

Horwich et al., "Synthesis of hepadenovirus particles that contain replication-defective duck hepatitis B virus genomes in cultured HuH7 cells," *J. Virol.*, 64:642–650, 1990.

Jones and Shenk, "Isolation of deletion and substitution mutants of adenovirus type 5," *Cell*, 13:181–188, 1978.

Kaneda et al., "Increased expression of DNA cointroduced with nuclear protein in adult rat liver," *Science*, 243:375–378, 1989.

Karlsson et. al., *EMBO J.*, 5:2377–2385, 1986.

Kato et al., "Expression of hepatitis β virus surface antigen in adult rat liver," *J. Biol. Chem.*, 266:3361–3364, 1991.

Kaufman, *Cancer Res.*, 49:5870–5878, 1989.

Klein et al., "High-velocity microprojectiles for delivering nucleic acids into living cells," *Nature*, 327:70–73, 1987.

Le Gal La Salle et al., "An adenovirus vector for gene transfer into neurons and glia in the brain," *Science* 259:988–990, 1993.

Levrero et al., "Defective and nondefective adenovirus vectors for expressing foreign genes in vitro and in vivo," *Gene*, 101:195–202, 1991.

MacGregor et al., *Somat Cell Mol. Genet.*, 13:253–265, 1987.

Mann et al., "Construction of a retrovirus packaging mutant and its use to produce helper-free defective retrovirus," *Cell*, 33:153–159, 1983.

Markowitz et al., "A safe packaging line for gene transfer: Separating viral genes on two different plasmids," *J. Virol.*, 62:1120–1124, 1988.

Mercer, "Cell cycle regulation and the p53 tumor suppressor protein," *Critic. Rev. Eukar. Gene Express.* 2:251–263, 1992.

Mietz et al., *EMBO*, 11:5013,5020,1992.

Mizrahi, "Production of human interferons: An overview," Process Biochem., (Aug.):9–12, 1983.

Mulligan, "The Basic Science of Gene Therapy," *Science*, 260:926–932, 1993.

Nguyen et al., *J. Virol.*, (submitted), 1996a.

Nguyen et al., Cancer Gene Ther., (submitted), 1996b.

Nicolas and Rubenstein, "Retroviral vectors," In: Vectors: A survey of molecular cloning vectors and their uses, Rodriguez and Denhardt (eds.), Stoneham: Butterworth, pp. 494–513, 1988.

Nicolau and Sene, "Liposome-mediated DNA transfer in eukaryotic cells," *Biochem. Biophys. Acta*, 721:185–190, 1982.

Nicolau et al., "Liposomes as carriers for in vivo gene transfer and expression," *Methods Enzymol.*, 149:157–176, 1987.

Paskind et al., "Dependence of moloney murine leukemia virus production on cell growth," *Virology*, 67:242–248, 1975.

Perales et al., *Proc. Natl. Acad. Sci. USA*, 91:4086–4090, 1994.

Phillips et al., In: *Large Scale Mammalian Cell Culture* (Feder, J. and Tolbert, W. R., eds.), Academic Press, Orlando, Fla., U.S.A., 1985.

Ponder et al., *Proc. Natl. Acad. Sci. USA*, 88:1217–1221, 1991.

Potter et al., "Enhancer-dependent expression of human k immunoglobulin genes introduced into mouse pre-B lymphocytes by electroporation," *Proc. Nat'l Acad. Sci. USA*, 81:7161–7165, 1984.

Ragot et al., "Efficient adenovirus-mediated transfer of a human minidystrophin gene to skeletal muscle of mdx mice," *Nature*, 361:647–650, 1993.

Renan, "Cancer genes: current status, future prospects, and applicants in radiotherapy/oncology," *Radiother. Oncol.*, 19:197–218, 1990.

Rich el al., "Development and analysis of recombinant adenoviruses for gene therapy of cystic fibrosis," *Hum. Gene Ther.*, 4:461–476, 1993.

Ridgeway, "Mammalian expression vectors," In: Rodriguez RL, Denbardt DT, ed. Vectors: A survey of molecular cloning vectors and their uses. Stoneham: Butterworth, pp. 467–492, 1988.

Rippe et al., "DNA-mediated gene transfer into adult rat hepatocytes in primary culture," *Mol. Cell Biol.*, 10:689–695, 1990.

Rosenfeld et al., "Adenovirus-mediated transfer of a recombinant a1-antitrypsin gene to the lung epithelium in vivo," *Science*, 252:431–434, 1991.

Rosenfeld et al., "In vivo transfer of the human cystic fibrosis transmembrane conductance regulator gene to the airway epithelium," *Cell*, 68:143–155, 1992.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Natl. Acad. Sci. USA*, 86:9079–9083, 1989.

Russell et al., *Proc. Natl. Acad. Sci. USA*, 92:5719–5723, 1995.

Shaw et al., 89:4495–4499, 1992.

Son & Huang, *Proc. Natl. Acad. Sci USA*, 91:12669–12672, 1994.

Stratford-Perricaudet and Perricaudet, "Gene transfer into animals: the promise of adenovirus," p. 51–61, In: *Human Gene Transfer*, Eds, O. Cohen-Haguenauer and M. Boiron, Editions John Libbey Eurotext, France, 1991.

Stratford-Perricaudet et al., "Evaluation of the transfer and expression in mice of an enzyme-encoding gene using a human adenovirus vector," *Hum. Gene Ther.*, 1:241–256, 1990.

Takahasi et al., "Wild-type but not mutant p53 suppresses the growth of human lung cancer cells bearing multiple genetic lesions," *Cancer Res.*, 52:2340–2342, 1992.

Temin, "Retrovirus vectors for gene transfer: Efficient integration into and expression of exogenous DNA in vertebrate cell genome," In: Gene Transfer, Kucherlapati (ed.), New York: Plenum Press, pp. 149–188, 1986.

Top et al., "Immunization with live types 7 and 4 adenovirus vaccines. II. Antibody response and protective effect against acute respiratory disease due to adenovirus type 7," *J. Infect. Dis.*, 124:155–160, 1971.

Tur-Kaspa et al., "Use of electroporation to introduce biologically active foreign genes into primary rat hepatocytes," *Mol. Cell Biol.*, 6:716–718, 1986.

Wagner et al., *Science*, 260:1510–1513, 1990.

Weinberg, "Tumor suppressor gene," *Science*, 254:1138–1145, 1991.

Wilcock and Lane, *Nature*, 349:429–431, 1991.

Wong et al., "Appearance of β-lactamase activity in animal cells upon liposome mediated gene transfer," *Gene*, 10:87–94, 1980.

Wu and Wu, "Receptor mediated in vitro gene transfections by a soluble DNA courier system," *J. Biol. Chem*, 262:4429–4432, 1987.

Wu and Wu, "Evidence for targeted gene delivery to HepG2 hepatoma cells in vitro," *Biochemistry*, 27:887–892, 1988.

Wu and Wu, Adv. *Drug Delivery Rev.*, 12:159–167, 1993.

Yang et al., "In vivo and in vitro gene transfer to mammalian somatic cells by particle bombardment," *Proc. Nat'l Acad. Sci. USA*, 87:9568–9572, 1990.

Yonish-Rouach et al., *Nature*, 352:345–347, 1991.

Varmus et al., "Retroviruses as mutagens: Insertion and excision of a non-transforming provirus alter the expression of a resident transforming provirus," *Cell*, 25:23–36, 1981.

Zakut-Houri et al., *EMBO J.*, 4:1251–2355, 1985.

Zelenin et al., "High-velocity mechanical DNA transfer of the chloramphenicol acetyltransferase gene into rodent liver, kidney and mammary gland cells in organ explants and in vivo," *FEBS Lett.*, 280:94–96, 1991.

Zhang et al., "Detection of Wild-type Contanination in a Recombinant Adenoviral Preparation by PCR™," *BioTechniques*, 18:5–8, 1995b.

Zhang et al., "Safety Evaluation of Ad5CMV-p53 In Vitro and In Vivo," *Human Gene Ther.*, 6:155–164, 1995a.

What is claimed is:

1. A method for enhancing the expression of a transgene in a target neoplastic cell in vivo comprising:

(a) administering a DNA-damaging agent to a subject containing a target neoplastic cell; and (b) transferring said transgene into said target neoplastic cell between 2–4 days after said administering step;

whereby expression of said transgene is enhanced as a result of the administering of said DNA-damaging agent to said target neoplastic cell.

2. The method of claim 1, wherein said target neoplastic cell is a dividing cell.

3. The method of claim 1, wherein said DNA-damaging agent is selected from the group consisting of cisplatin, carboplatin, VP16, teniposide, daunorubicin, doxorubicin, dactinomycin, mitomycin, plicamycin, bleomycin, procarbazine, nitrosourea, cyclophosphamide, bisulfan, melphalan, chlorambucil, ifosfamide, merchlorehtamine, and ionizing radiation.

4. The method of claim 1, wherein said transgene is transferred at about 3 days after said administering step.

5. The method of claim 1, wherein said transfer of said transgene is accomplished by a technique selected from the group consisting of liposome-mediated transfection, receptormediated internalization and viral infection.

6. The method of claim 1, wherein said transgene encodes a tumor suppressor.

7. The method of claim 6, wherein said tumor suppressor is p53.

8. The method of claim 7, wherein said p53 transgene is under the transcriptional control of a CMV IE promoter.

9. The method of claim 3, wherein said DNA-damaging agent is cisplatin.

10. The method of claim 7, wherein said p53 transgene is carried in an adenoviral vector.

* * * * *

UNITED STATES PATENT AND TRADEMARK OFFICE
CERTIFICATE OF CORRECTION

PATENT NO.   : 6,271,207 B1
DATED        : August 7, 2001
INVENTOR(S)  : Richard J. Cristiano and Dao Nguyen It is certified that error appears in the above-identified patent and that said Letters Patent is hereby corrected as shown below:

<u>Title page,</u>
Item [75], line 2, please delete "Potamac" and insert -- Potomac -- therefor.

<u>Column 34, claim 10,</u>
Line 52, please delete "receptormediated" and insert -- receptor-mediated -- therefor Signed and Sealed this Ninth Day of April, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

| | |
|---|---|
| PATENT NO. | : 6,271,207 B1 |
| APPLICATION NO. | : 09/175056 |
| DATED | : August 7, 2001 |
| INVENTOR(S) | : Richard J. Cristiano and Dao Nguyen |

It is certified that error appears in the above-identified patent and that said Letters Patent is hereby corrected as shown below:

In claim 3, column 34, line 44, delete "bisulfan" and insert--busulfan--therefor.

In claim 3, column 34, line 45, delete "merchlorethamine" and insert--mechlorethamine--therefor.

Signed and Sealed this

Second Day of January, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,271,207 B1 | Page 1 of 1 |
| APPLICATION NO. | : 09/175056 | |
| DATED | : August 7, 2001 | |
| INVENTOR(S) | : Richard J. Cristiano and Dao Nguyen | |

It is certified that error appears in the above-identified patent and that said Letters Patent is hereby corrected as shown below:

Col. 1, Line 7 delete "The government may own rights in the present invention pursuant to funding of research under NIH Grant No. CA66037-01." and insert -- This invention was made with government support under Grant No. CA66037-01 awarded by National Institute of Health. The government has certain rights in the invention --.

In claim 3, column 34, line 44, delete "bisulfan" and insert--busulfan--therefor.

In claim 3, column 34, line 45, delete "merchlorethamine" and insert--mechlorethamine--therefor.

Signed and Sealed this

Twenty-fifth Day of December, 2007

JON W. DUDAS
*Director of the United States Patent and Trademark Office*

UNITED STATES PATENT AND TRADEMARK OFFICE
CERTIFICATE OF CORRECTION

PATENT NO. : 6,271,207 B1 Page 1 of 1
APPLICATION NO. : 09/175056
DATED : August 7, 2001
INVENTOR(S) : Richard J. Cristiano and Dao Nguyen It is certified that error appears in the above-identified patent and that said Letters Patent is hereby corrected as shown below:

In item 75, line 2, please delete "Potamac" and insert --Potomac-- therefor.

In claim 10, column 34, line 52, please delete "receptormediated" and insert --receptor-mediated-- therefor.

Signed and Sealed this

Twenty-sixth Day of February, 2008

JON W. DUDAS
*Director of the United States Patent and Trademark Office*